(12) United States Patent
Kato et al.

(10) Patent No.: US 9,595,101 B2
(45) Date of Patent: Mar. 14, 2017

(54) X-RAY CT APPARATUS, IMAGE PROCESSING APPARATUS, AND IMAGE PROCESSING METHOD

(71) Applicant: Toshiba Medical Systems Corporation, Otawara-shi (JP)

(72) Inventors: Tooru Kato, Nasushiobara (JP); Daizo Oikawa, Otawara (JP); Hiroaki Nakai, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/744,645

(22) Filed: Jun. 19, 2015

(65) Prior Publication Data

US 2015/0287193 A1    Oct. 8, 2015

Related U.S. Application Data

(63) Continuation of application No. PCT/JP2013/084144, filed on Dec. 19, 2013.

(30) Foreign Application Priority Data

Dec. 19, 2012 (JP) .................................. 2012-276981
Dec. 19, 2013 (JP) .................................. 2013-262778

(51) Int. Cl.
  *G06T 7/00* (2006.01)
  *A61B 6/03* (2006.01)
  (Continued)

(52) U.S. Cl.
  CPC ............ *G06T 7/0012* (2013.01); *A61B 6/032* (2013.01); *A61B 6/4241* (2013.01); *A61B 6/482* (2013.01);
  (Continued)

(58) Field of Classification Search
  None
  See application file for complete search history.

(56) References Cited

U.S. PATENT DOCUMENTS

| 7,663,120 B2 * | 2/2010 | Tomita ................... G01T 1/247 250/394 |
| 8,213,566 B2 | 7/2012 | Roessl et al. |

(Continued)

FOREIGN PATENT DOCUMENTS

| CN | 102088907 A | 6/2011 |
| JP | 2000-069369 A | 3/2000 |

(Continued)

OTHER PUBLICATIONS

English Translation of the International Search Report issued Mar. 25, 2014 in PCT/JP2013/084144 filed Dec. 19, 2013.
Written Opinion issued Mar. 25, 2014 in PCT/JP2013/084144 filed Dec. 19, 2013 with English translation.
Chinese Office Action mailed Dec. 5, 2016 in Chinese Patent Application No. 201380052081.3.

*Primary Examiner* — Vu Le
*Assistant Examiner* — Delomia L Gilliard
(74) *Attorney, Agent, or Firm* — Oblon, McClelland, Maier & Neustadt, L.L.P.

(57) ABSTRACT

An X-ray CT apparatus according to an embodiment includes acquiring circuitry and processing circuitry. The acquiring circuitry is configured to count photons derived from X-rays that have passed through a subject and to acquire a result obtained by discriminating energy levels of the counted photons as a counting result. The processing circuitry is configured to notify the acquiring circuitry of an energy dividing set that is set in accordance with an X-ray absorption characteristic of a substance designated by an operator, to receive the counting result acquired by the acquiring circuitry by allocating a counted value to each of (Continued)

a plurality of energy discrimination regions that are set in the energy dividing set, and to reconstruct image data by using the received counting result.

11 Claims, 14 Drawing Sheets

(51) Int. Cl.
*A61B 6/00* (2006.01)
*G06T 11/00* (2006.01)
*G06K 9/46* (2006.01)
*G06T 5/00* (2006.01)

(52) U.S. Cl.
CPC .............. *A61B 6/5205* (2013.01); *G06K 9/46* (2013.01); *G06T 5/001* (2013.01); *G06T 11/005* (2013.01); *G06K 2009/4666* (2013.01); *G06T 2207/10081* (2013.01); *G06T 2207/10116* (2013.01); *G06T 2211/408* (2013.01)

(56) References Cited

U.S. PATENT DOCUMENTS

| | | | |
|---|---|---|---|
| 2011/0096905 A1* | 4/2011 | Roessl | A61B 5/4869 378/62 |
| 2011/0116594 A1* | 5/2011 | Yamakawa | A61B 6/032 378/19 |
| 2012/0087463 A1 | 4/2012 | Greenberg et al. | |
| 2014/0328465 A1* | 11/2014 | Herrmann | G01T 1/17 378/62 |

FOREIGN PATENT DOCUMENTS

| | | |
|---|---|---|
| JP | 2009-014624 A | 1/2009 |
| JP | 2011-527223 A | 10/2011 |
| JP | 2012-034901 A | 2/2012 |
| WO | WO 2012/049682 A2 | 4/2012 |

* cited by examiner

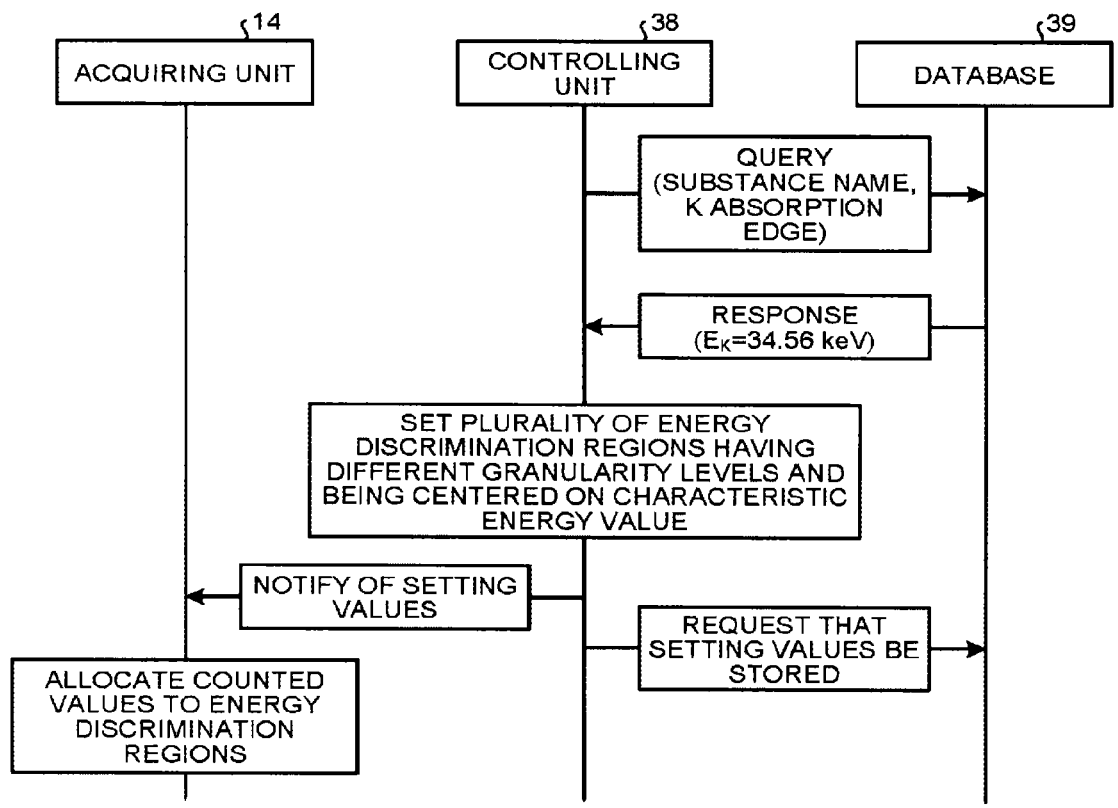

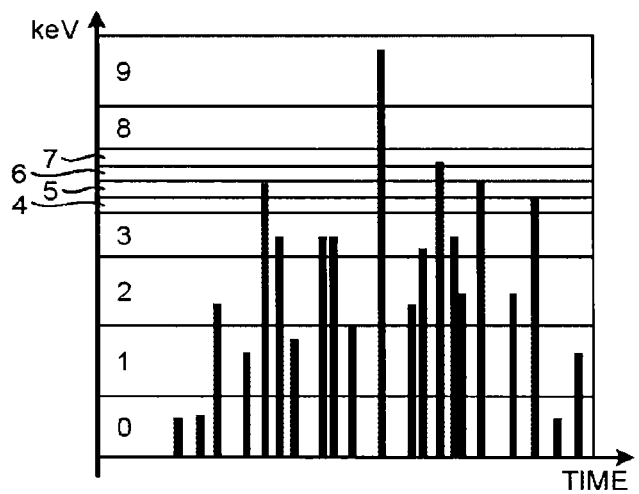
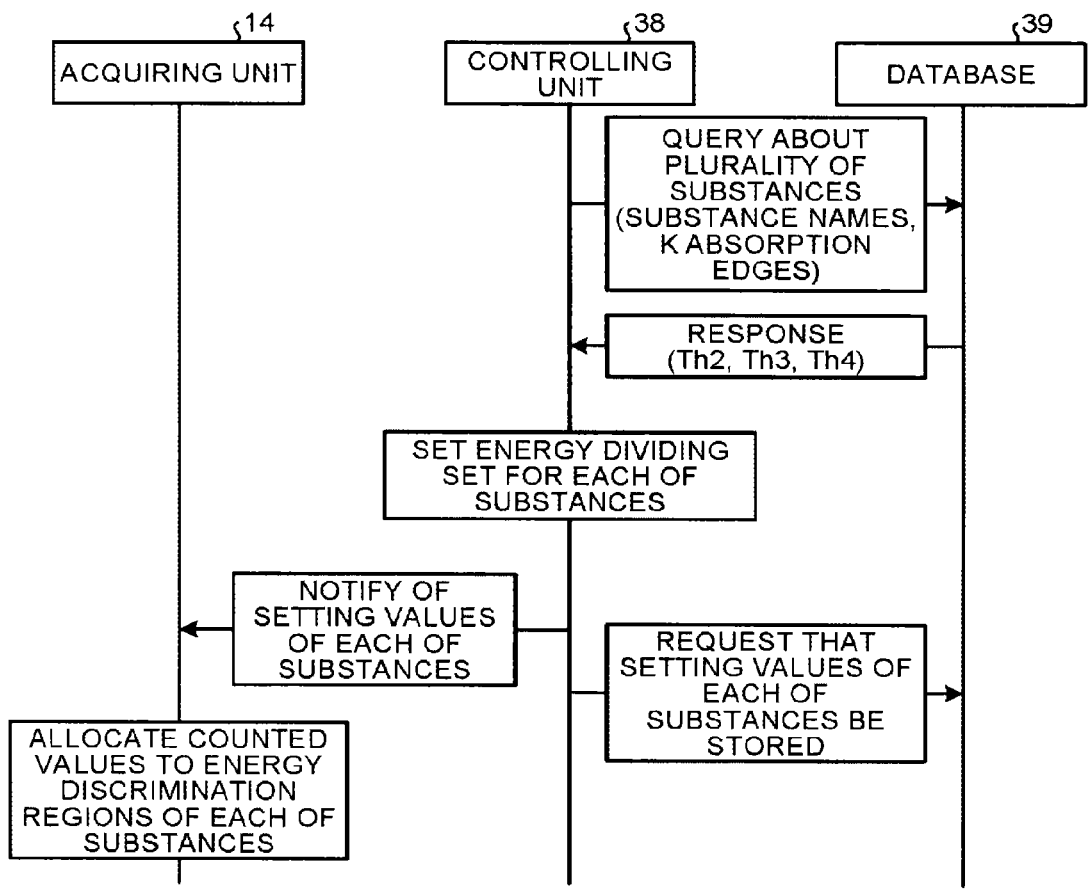

X-RAY CT APPARATUS, IMAGE PROCESSING APPARATUS, AND IMAGE PROCESSING METHOD

CROSS-REFERENCE TO RELATED APPLICATIONS

This application is a continuation of PCT international application Ser. No. PCT/JP2013/084144 filed on Dec. 19, 2013 which designates the United States, incorporated herein by reference, and which claims the benefit of priority from Japanese Patent Application No. 2012-276981, filed on Dec. 19, 2012 and Japanese Patent Application No. 2013-262778, filed on Dec. 19, 2013, the entire contents of which are incorporated herein by reference.

FIELD

Embodiments described herein relate generally to an X-ray Computed Tomography (CT) apparatus, an image processing apparatus, and an image processing method.

BACKGROUND

In recent years, X-ray CT apparatuses that perform a photon counting Computed Tomography (CT) by employing a photon-counting type detector have been developed. Unlike integral-type detectors used in conventional X-ray CT apparatuses, the photon-counting type detector outputs signals that make it possible to individually count photons derived from X-rays that have passed through an examined subject (hereinafter, a "subject"). Accordingly, by performing the photon counting CT, it is possible to reconstruct an X-ray CT image having a high Signal-per-Noise (S/N) ratio.

Further, the signals output by the photon-counting type detector can be used for measuring (discriminating) an energy level of each of the counted photons. Accordingly, by performing the photon counting CT, it is possible to image data acquired by radiating X-rays while using one type of X-ray tube voltage in such a manner that the data is divided into a plurality of energy components. For example, by performing the photon counting CT, it is possible to generate an image that makes it possible to identify one or more substances by utilizing differences in K absorption edges. Examples of the substances include contrast agents and chemical labeling substances that are able to specifically label tissues.

As explained here, by performing the photon counting CT, it is possible to generate the image that makes it possible to identify the substances of interest, by discriminating the individual photons so as to be divided into the energy components. However, if the energy discrimination is finely performed, the amount of data becomes extremely large, and it takes a long time to transfer data and perform the reconstruction. On the contrary, if the energy discrimination is roughly performed, it is not possible to obtain the data necessary for identifying the substances of interest.

BRIEF DESCRIPTION OF THE DRAWINGS

FIG. 5A and FIG. 5B are drawings of examples of data structures stored in the database illustrated in FIG. 1;

FIG. 6, FIG. 7 and FIG. 8 are drawings for explaining a controlling process performed by a controlling unit according to the first embodiment, on the basis of a first setting method;

FIG. 9 is a drawing for explaining a controlling process performed by the controlling unit according to the first embodiment when a plurality of substances is designated;

DETAILED DESCRIPTION

Figure 1:
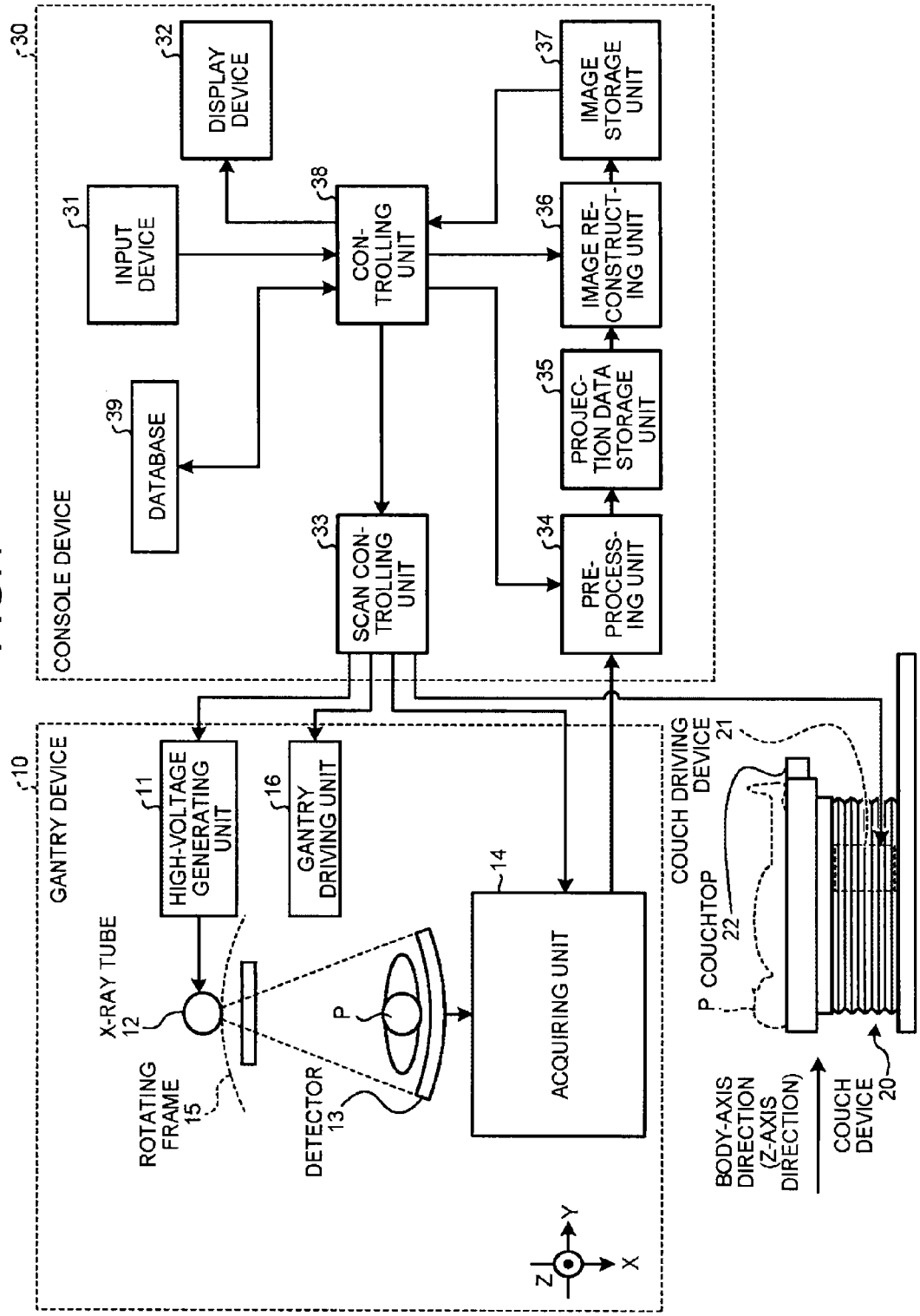
FIG. 1 is a diagram of an exemplary configuration of an X-ray CT apparatus according to a first embodiment.

An X-ray CT apparatus according to an embodiment includes acquiring circuitry and processing circuitry. The acquiring circuitry is configured to count photons derived from X-rays that have passed through a subject and to acquire a result obtained by discriminating energy levels of the counted photons as a counting result. The processing circuitry is configured to notify the acquiring circuitry of an energy dividing set that is set in accordance with an X-ray absorption characteristic of a substance designated by an operator, to receive the counting result acquired by the acquiring circuitry by allocating a counted value to each of a plurality of energy discrimination regions that are set in the energy dividing set, and to reconstruct image data by using the received counting result.

An X-ray CT apparatus according to an embodiment includes an acquiring unit, a controlling unit, and an image reconstructing unit. The acquiring unit counts photons derived from X-rays that have passed through a subject and acquires a result obtained by discriminating energy levels of the counted photons as a counting result. The controlling unit notifies the acquiring unit of an energy dividing set that is set in accordance with an X-ray absorption characteristic of a substance designated by an operator. The image reconstructing unit receives the counting result acquired by the acquiring unit by allocating a counted value to each of a plurality of energy discrimination regions that are set in the energy dividing set and reconstructs image data by using the received counting result.

Exemplary embodiments of an X-ray Computed Tomography (CT) apparatus will be explained in detail, with reference to the accompanying drawings.

The X-ray CT apparatuses explained in the exemplary embodiments below are capable of performing a photon counting CT. In other words, the X-ray CT apparatuses explained in the exemplary embodiments below are each capable of reconstructing X-ray CT image data having a high S/N ratio, by counting X-rays that have passed through a subject by employing a photon-counting type detector, instead of a conventional integral-type detector (that uses a current mode measuring method).

During the photon counting CT, the amount of light (X-rays) is measured by counting the number of photons. The larger the number of photons per unit time is, the stronger the light (the X-rays) is. Further, although each photon has a different level of energy, the photon counting CT makes it possible to obtain information about energy components of the X-rays by measuring the energy of the photons. In other words, by performing the photon counting CT, it is possible to image data acquired by radiating X-rays while using one type of X-ray tube voltage in such a manner that the data is divided into a plurality of energy components.

In this situation, absorption edges serve as energy components that are unique to each substance. The energy of an absorption edge (a K absorption edge or an L absorption edge) is determined by the absorbing atoms, the quantum number of inner-shell electrons that are excited, and the electron configuration in the valence band. For example, by performing the photon counting CT, it is possible to obtain image data that makes it possible to identify substances by utilizing differences in the K absorption edges.

First Embodiment

First, a configuration of an X-ray CT apparatus according to a first embodiment will be explained. FIG. 1 is a diagram of an exemplary configuration of the X-ray CT apparatus according to the first embodiment. As illustrated in FIG. 1, the X-ray CT apparatus according to the first embodiment includes a gantry device 10, a couch device 20, and a console device 30.

The gantry device 10 is a device that radiates X-rays to a subject P and counts X-rays that have passed through the subject P. The gantry device 10 includes a high-voltage generating unit 11, an X-ray tube 12, a detector 13, an acquiring unit 14, a rotating frame 15, and a gantry driving unit 16.

The rotating frame 15 is an annular frame that supports the X-ray tube 12 and the detector 13 so as to face each other while the subject P is interposed therebetween and that is rotated by the gantry driving unit 16 (explained later) at a high speed on a circular trajectory centered on the subject P.

The X-ray tube 12 is a vacuum tube that radiates the X-ray beams to the subject P by using a high voltage supplied by the high-voltage generating unit 11 (explained later). In conjunction with rotations of the rotating frame 15, the X-ray tube 12 radiates the X-ray beams onto the subject P.

The high-voltage generating unit 11 is a device that supplies the high voltage to the X-ray tube 12. The X-ray tube 12 generates the X-rays by using the high voltage supplied from the high-voltage generating unit 11. In other words, the high-voltage generating unit 11 adjusts the dose of the X-rays radiated to the subject P, by adjusting an X-ray tube voltage and an X-ray tube current supplied to the X-ray tube 12.

By driving the rotating frame 15 to rotate, the gantry driving unit 16 causes the X-ray tube 12 and the detector 13 to turn on the circular trajectory centered on the subject P.

The detector 13 includes a plurality of detecting elements that count light beams derived from the X-rays that have passed through the subject P. In one example, the detecting elements included in the detector 13 according to the first embodiment are cadmium-telluride-based semiconductors.

In other words, the detector 13 according to the first embodiment is a direct-conversion-type semiconductor detector that counts the light beams derived from the X-rays by directly converting the incident X-rays to the light beams.

Figure 2:
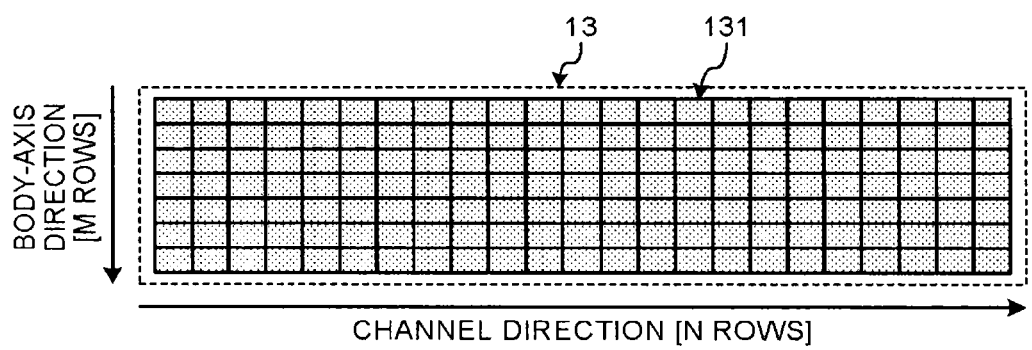
FIG. 2 is a drawing for explaining an example of a detector according to the first embodiment.

FIG. 2 is a drawing for explaining an example of the detector according to the first embodiment. For example, the detector 13 according to the first embodiment is, as illustrated in FIG. 2, an area detector in which detecting elements 131 formed with cadmium telluride are arranged in N rows along the channel direction (the Y-axis direction in FIG. 1) and are arranged in M rows along the body-axis direction (the Z-axis direction in FIG. 1). When a photon has become incident thereto, each of the detecting elements 131 outputs an electric signal of one pulse. By discriminating each of the pulses output by the detecting elements 131, it is possible to count the number of photons (X-ray photons) derived from the X-rays that have become incident to the detecting elements 131. Further, by performing a calculating process based on the strength of each of the pulses, it is possible to measure the energy levels of the counted photons.

In the following sections, an example will be explained in which the detector 13 is a direct-conversion-type semiconductor detector; however, for example, the first embodiment is also applicable to a situation where an indirect-conversion-type detector configured with scintillators and photomultiplier tubes is used as the detector 13.

The acquiring unit 14 acquires a counting result, which is the result of the counting process performed by using the output signals from the detector 13. The acquiring unit 14 counts the photons (the X-ray photons) derived from the X-rays that were radiated from the X-ray tube 12 and that have passed through the subject P and acquires the result obtained by discriminating the energy levels of the counted photons as a counting result. After that, the acquiring unit 14 transmits the counting result to the console device 30.

Specifically, the acquiring unit 14 acquires, for each of phases of the X-ray tube 12 (X-ray tube phases), incident positions (detection positions) of the X-ray photons counted by discriminating the pulses output by the detecting elements 131 and an energy value of the X-ray photons, as the counting result. For example, the acquiring unit 14 uses the positions of the detecting elements 131 that output the pulses used in the counting process as the incident positions. Further, for example, the acquiring unit 14 calculates the energy value from a peak value of the pulses and a response function unique to the system. Alternatively, for example, the acquiring unit 14 may calculate the energy value by integrating the strengths of the pulses. The acquiring unit 14 allocates the calculated energy value (E) to a plurality of energy discrimination regions.

The acquiring unit 14 according to the first embodiment allocates the calculated energy value to the plurality of energy discrimination regions by using a comparator, for example. The plurality of energy discrimination regions serve as an energy dividing set that is set by using threshold values, so that the acquiring unit 14 is able to discriminate and allocate the energy value to energy ranges having predetermined granularity levels.

For example, the counting result acquired by the acquiring unit 14 may be information indicating that "in a X-ray tube phase "α1", the counted value of photons in the energy discrimination region "E1<E≤E2" is "N1", whereas the counted value of photons in the energy discrimination region "E2<E≤E3" is "N2", at the detecting element 131 in an incident position "P11"". Alternatively, the counting result acquired by the acquiring unit 14 may be information indicating that "in a X-ray tube phase "α1", the counted value of photons per unit time in the energy discrimination region "E1<E≤E2" is "n1", whereas the counted value of photons per unit time in the energy discrimination region "E2<E≤E3" is "n2", at the detecting element 131 in an incident position "P11"".

The couch device 20 is a device on which the subject P is placed and includes a couchtop 22 and a couch driving device 21. The couchtop 22 is a plate on which the subject P is placed. The couch driving device 21 moves the couchtop 22 in the Z-axis direction so as to move the subject P into the rotating frame 15.

For example, the gantry device 10 performs a helical scan, which is to helically scan the subject P by causing the rotating frame 15 to rotate while moving the couchtop 22. In another example, the gantry device 10 performs a conventional can, which is to scan the subject P on the circular trajectory by causing the rotating frame 15 to rotate while the subject P is fixed in a position after the couchtop 22 has been moved. In yet another example, the gantry device 10 implements a step-and-shoot method by which the conventional scan is performed in a plurality of scan areas by moving the couchtop 22 to positions arranged at regular intervals.

The console device 30 is a device that receives an operation performed on the X-ray CT apparatus by an operator and reconstructs X-ray CT image data by using the counting result acquired by the gantry device 10. As illustrated in FIG. 1, the console device 30 includes an input device 31, a display device 32, a scan controlling unit 33, a preprocessing unit 34, a projection data storage unit 35, an image reconstructing unit 36, an image storage unit 37, a controlling unit 38, and a database 39.

The input device 31 includes a mouse, a keyboard, and the like used by the operator of the X-ray CT apparatus to input various types of instructions and various types of settings. The input device 31 transfers information about the instructions and the settings received from the operator to the controlling unit 38. For example, the input device 31 receives, from the operator, a reconstructing condition used for reconstructing the X-ray CT image data, an image processing condition for the X-ray CT image data, and the like.

The display device 32 is a monitor referred by the operator. Under control of the controlling unit 38, the display device 32 displays the X-ray CT image data for the operator and displays a Graphical User Interface (GUI) used for receiving the various types of instructions and the various types of settings from the operator via the input device 31. The GUI displayed in the first embodiment will be explained in detail later.

Under the control of the controlling unit 38 (explained later), the scan controlling unit 33 controls count information acquiring processes performed by the gantry device 10, by controlling the operations of the high-voltage generating unit 11, the gantry driving unit 16, the acquiring unit 14, and the couch driving device 21.

The preprocessing unit 34 generates projection data by performing a correcting process such as a logarithmic transformation process, an offset correction, a sensitivity correction, a beam hardening correction, and/or the like, on the counting result transmitted from the data acquiring unit 14.

The projection data storage unit 35 stores the projection data generated by the preprocessing unit 34. In other words, the projection data storage unit 35 stores the projection data (the counting result) used for reconstructing the X-ray CT image data.

The image reconstructing unit 36 reconstructs the X-ray CT image data by, for example, performing a back-projection process on the projection data stored in the projection data storage unit 35. Examples of the back-projection process include one that uses a Filtered Back Projection (FBP) method. Alternatively, the image reconstructing unit 36 may perform the reconstructing process by implementing a successive approximation method or the like. Further, the image reconstructing unit 36 generates image data by performing various types of image processing on the X-ray CT image data. The image reconstructing unit 36 stores the reconstructed X-ray CT image data and the image data generated by performing the various types of image processing, in the image storage unit 37.

In this situation, the projection data generated from the counting result obtained from the photon counting CT contains information about the energy of the X-rays attenuated by passing through the subject P. For this reason, the image reconstructing unit 36 is able to, for example, reconstruct X-ray CT image data representing a specific energy component. Further, the image reconstructing unit 36 is able to, for example, reconstruct X-ray CT image data representing each of a plurality of energy components.

Further, for example, the image reconstructing unit 36 is able to generate image data in which a tone corresponding to an energy component is assigned to each of the pixels in the X-ray CT image data representing the energy components, so that a plurality of pieces of X-ray CT image data that are color-coded associated with the energy components are superimposed. Further, the image reconstructing unit 36 is able to generate image data that makes it possible to identify substances by utilizing the K absorption edge unique to each substance. Other examples of image data generated by the image reconstructing unit 36 include monochrome X-ray image data, density image data, and effective atomic number image data.

The database 39 is a storage unit that stores information about the X-ray absorption spectrum of each of a plurality of substances. In other words, the database 39 is a database storing analytical chemical information. The database 39 is able to update and store various types of analytical chemical information, by using information from external analytical chemical databases.

The controlling unit 38 exercises overall control of the X-ray CT apparatus, by controlling the operations of the gantry device 10, the couch device 20, and the console device 30. Specifically, the controlling unit 38 controls a CT scan performed by the gantry device 10, by controlling the scan controlling unit 33. Further, the controlling unit 38 controls the image reconstructing process and the image generating process performed by the console device 30, by controlling the preprocessing unit 34 and the image reconstructing unit 36. Further, the controlling unit 38 exercises control so that the various types of image data stored in the image storage unit 37 are displayed on the display device 32. The controlling processes performed by the controlling unit 38 in the first embodiment will be explained in detail later.

An overall configuration of the X-ray CT apparatus according to the first embodiment has thus been explained. The X-ray CT apparatus according to the first embodiment configured as described above performs the image data reconstructing process and the image data generating process that utilize the energy components unique to each substance, by performing the photon counting CT.

Figure 3:
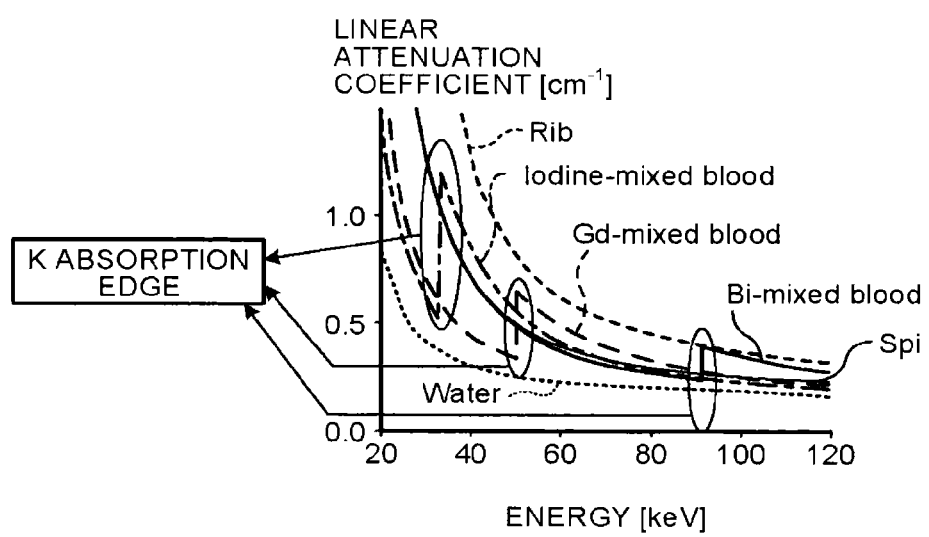
FIG. 3 is a drawing for explaining K absorption edges.

Next, the K absorption edges, which serve as an example of the energy components unique to each substance, will be explained, with reference to FIG. 3. FIG. 3 is a drawing for explaining the K absorption edges. FIG. 3 illustrates X-ray absorption spectra of various substances. The horizontal axis in FIG. 3 expresses energy (unit: keV), whereas the vertical axis in FIG. 3 expresses linear attenuation coefficient (unit: $cm^{-1}$).

FIG. 3 illustrates an X-ray absorption spectrum of blood ("Iodine-mixed blood") that has an iodine-based contrast agent mixed therein; an X-ray absorption spectrum of blood ("Gd-mixed blood") that has a gadolinium-based contrast agent mixed therein; and an X-ray absorption spectrum of blood ("Bi-mixed blood") that has a bismuth-based contrast agent mixed therein. Further, FIG. 3 also illustrates X-ray absorption spectra of water ("Water"), the lower extremity ("Rib"), and the spine ("Spi").

As illustrated in FIG. 3, the attenuation coefficient rapidly rises before and after a K absorption edge. For example, when iodine of which the K absorption edge is at "33.16 keV" is used as a substance of interest, the counted value of X-ray photons that have passed through tissues in which the iodine-based contrast agent is present is significantly different between the energy ranges positioned before and after "33.16 keV". For this reason, when identifying substances by utilizing the differences in the K absorption edges, the image reconstructing unit 36 reconstructs X-ray CT image data (hereinafter, "first image data") from the counting result (the projection data) in an energy discrimination region having a smaller value than the K absorption edge, for example. Further, the image reconstructing unit 36 reconstructs X-ray CT image data (hereinafter, "second image data") from the counting result (the projection data) in an energy discrimination region having a larger value than the K absorption edge, for example. After that, by subtracting the first image data from the second image data, the image reconstructing unit 36 generates difference image data. The difference image data primarily renders a region having a significantly-different counted value (e.g., the tissues in which the iodine-based contrast agent is present).

Figure 4A:
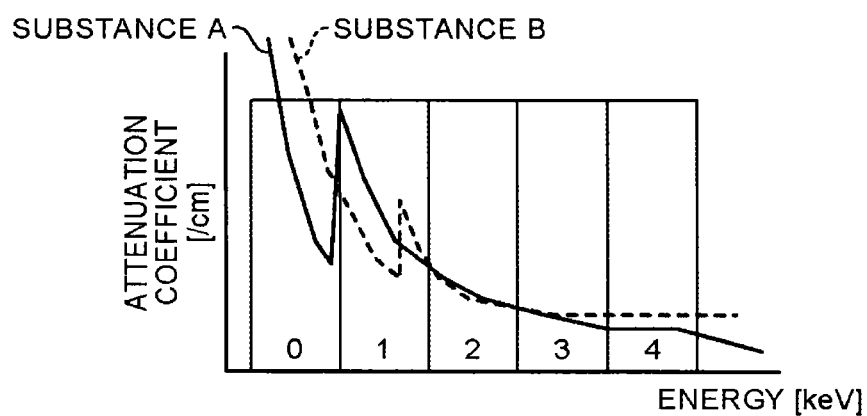
FIG. 4A and FIG. 4B are drawings for explaining problems of a conventional technique.
Figure 4B:
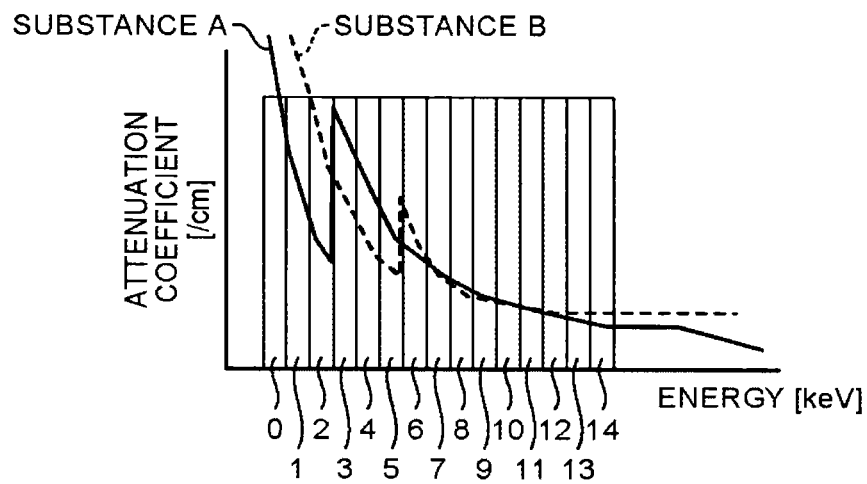

However, if the energy discrimination is finely performed, the amount of data becomes extremely large, and it takes a long time to transfer data and perform the reconstruction. On the contrary, if the energy discrimination is roughly performed, it is not possible to obtain the data necessary for identifying the substance of interest. These circumstances will be explained with reference to FIG. 4A and FIG. 4B. FIG. 4A and FIG. 4B are drawings for explaining problems of a conventional technique. FIG. 4A illustrates energy discrimination regions that are set by using a coarse granularity level, whereas FIG. 4B illustrates energy discrimination regions that are set by using a fine granularity level. FIG. 4A and FIG. 4B each illustrate X-ray absorption spectra of two mutually-different substances (a substance A and a substance B).

As illustrated in FIG. 4A, when five energy discrimination regions (0 to 4) having an equal width are set by using a coarse granularity level, it is possible to reduce the amount of the data obtained as the counting result. However, because the energy range of each of the five energy discrimination regions is so large that the image data generated from the counting result of each of the energy discrimination regions has a low capability for the substance discrimination. For example, the energy discrimination region (0) and the energy discrimination region (1) illustrated in FIG. 4A are divided by using the energy value of the K absorption edge of the substance A as the boundary. Thus, it is possible to generate difference image data that makes it possible to identify the substance A, by using the counting result of the energy discrimination region (0) and the counting result of the energy discrimination region (1). Meanwhile, for example, the energy value of the K absorption edge of the substance B is included in the vicinity of the center of the energy discrimination region (1) illustrated in FIG. 4A. Thus, even if difference image data is generated by using the counting result of the energy discrimination region (1) and the counting result of the energy discrimination region (2), the generated difference image data does not make it possible to identify the substance B.

In contrast, when fifteen energy discrimination regions (0 to 14) having an equal width are set by using a fine granularity level, as illustrated in FIG. 4B, because the energy range of each of the fifteen energy discrimination regions is small enough, the image data generated from the counting result of each of the energy discrimination regions has a high capability for the substance discrimination. For example, it is possible to generate difference image data that makes it possible to identify the substance A, by using the counting result of the energy discrimination region (2) and the counting result of the energy discrimination region (3) illustrated in FIG. 4B. Further, it is possible to generate difference image data that makes it possible to identify the substance B, by using the counting result of the energy discrimination region (5) and the counting result of the energy discrimination region (6) illustrated in FIG. 4B. However, when many energy discrimination regions are set by using the fine granularity level as illustrated in FIG. 4B, the amount of the data obtained as the counting results becomes large.

As explained above, in the conventional example, if the energy discrimination regions are coarsely set so as to reduce the amount of the data used in the imaging process, there may be some situations where it is not possible to secure the data that is required by the imaging process of a substance in which the operator is interested (hereinafter, a "substance of interest of the operator"). On the contrary, in the conventional example, if the energy discrimination regions are finely set so as to secure the data that is required by the imaging process of a substance of interest of the operator, the amount of the data used in the imaging process becomes large.

To cope with these situations, the controlling unit 38 according to the first embodiment exercises control over the acquiring unit 14 in the following manner, for the purpose of reducing the amount of the data used in the imaging process, while securing the data required by the imaging process of a substance of interest of the operator.

Specifically, for the acquiring unit 14, the controlling unit 38 sets an energy dividing set in accordance with X-ray absorption characteristics of a substance designated by the operator. After that, the controlling unit 38 notifies the acquiring unit 14 of the energy dividing set that was set. In this situation, the controlling unit 38 sets the energy dividing set prior to the acquisition of the counting result.

Under such control, the acquiring unit 14 acquires a counting result by allocating a counted value to each of a plurality of energy discrimination regions that are set in the energy dividing set and transmits the acquired counting result to the gantry device 10. Subsequently, the image reconstructing unit 36 reconstructs image data by using the counting result received from the acquiring unit 14. The image reconstructing unit 36 reconstructs the image data by using the projection data generated from the counting result received from the acquiring unit 14.

In other words, according to the first embodiment, the controlling unit 38 actively sets the energy dividing set in accordance with the X-ray absorption characteristics of the substance of interest of the operator. In other words, the controlling unit 38 sets the energy dividing set that is structured by the plurality of energy discrimination regions capable of securing the information required by the imaging process of the substance of interest of the operator, while keeping the number of energy discrimination regions small.

In this situation, for example, the X-ray absorption characteristics of a substance designated by the operator may be represented by a characteristic energy value (e.g., the K absorption edge) that is unique to the substance. The characteristic energy value such as the K absorption edge may be input by the operator. However, in order to perform the input operation, the operator needs to find out the characteristic energy value of the substance of interest of his/her own. In the first embodiment, although the operator may input the characteristic energy value that is unique to the substance, the database 39 described above is installed for the purpose of reducing the burden on the operator. In other words, the controlling unit 38 sets the energy dividing set described above, by using the database 39 storing the information about the X-ray absorption spectrum of each of the plurality of substances.

In this situation, if a single substance is designated by the operator, the controlling unit 38 according to the first embodiment sets the energy dividing set on the basis of a first setting method. If two or more substances are designated by the operator, the controlling unit 38 according to the first embodiment sets the energy dividing set on the basis of either a second setting method or a third setting method obtained by combining the first setting method with the second setting method.

Figure 7:
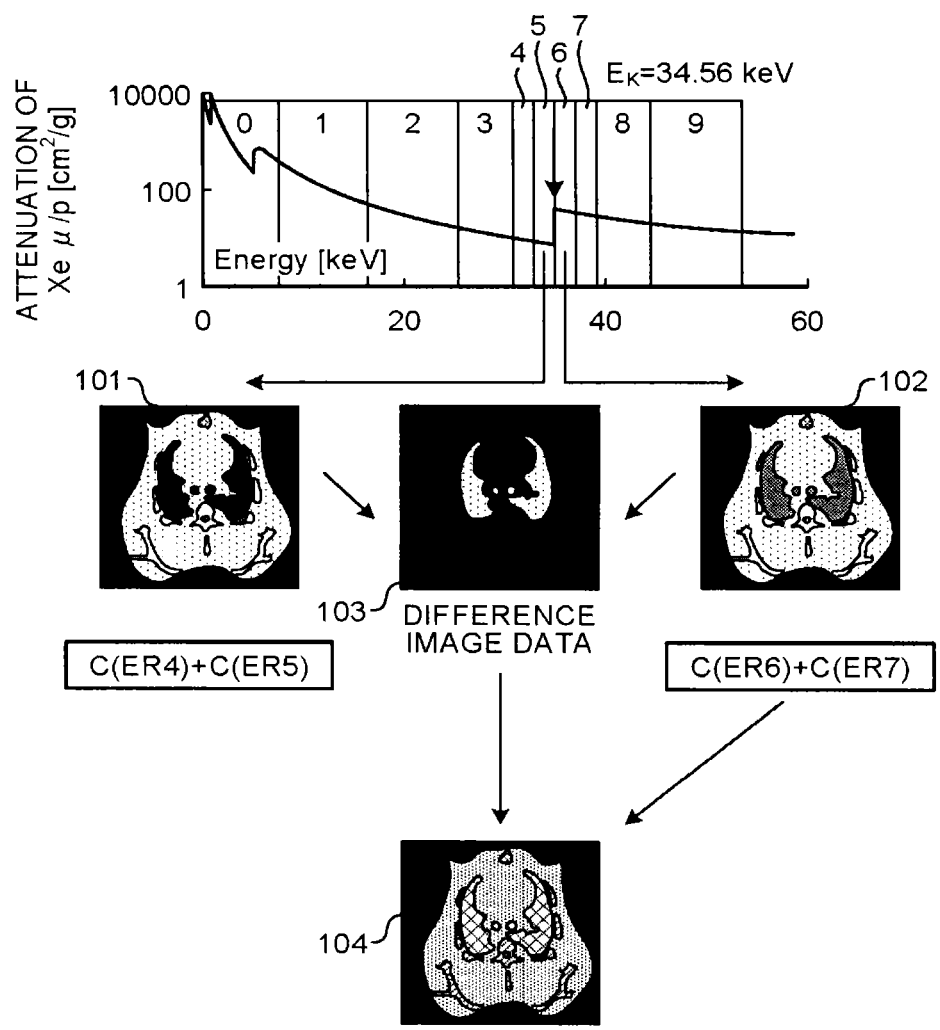

First, a controlling process performed by the controlling unit 38 on the basis of the first setting method will be explained, with reference to FIG. 5A, FIG. 5B, FIG. 6, and FIG. 7. FIG. 5A and FIG. 5B are drawings of examples of data structures stored in the database illustrated in FIG. 1. FIG. 6 and FIG. 7 are drawings for explaining the controlling process performed by the controlling unit according to the first embodiment, on the basis of the first setting method. The controlling process explained below is applied when difference image data that makes it possible to identify the substances by utilizing the differences in the K absorption edges is to be generated.

First, when having received an input of a parameter that makes it possible to identify a substance from the operator, the controlling unit 38 obtains a characteristic energy value that is unique to the substance corresponding to the received parameter, by referring to the database 39. In other words, the controlling unit 38 performs a process to search for an energy component that is unique to the substance, by using the database 39.

For example, as illustrated in FIG. 5A, the database 39 stores "substance name: A", "product name: A'", and "X-ray absorption spectrum: S(A)" so as to be associated with one another. The database 39 illustrated in FIG. 5A has a data structure in which the X-ray absorption spectrum of each of the plurality of substances is associated with the substance name and the product name, which are parameters that make it possible to identify the substance.

Alternatively, as illustrated in FIG. 5B, the database 39 stores "substance name: A", "product name: A'", "K absorption edge: $E_K(A)$" and "L absorption edge: $E_L(A)$" so as to be associated with one another. The database 39 illustrated in FIG. 5B has a data structure in which a characteristic energy value that characterizes the X-ray absorption spectrum of each of the plurality of substances is associated with the substance name and the product name, which are parameters that make it possible to identify the substance.

As explained here, the database 39 stores one or both of an X-ray absorption coefficient and a characteristic energy value of each of the substances (including contrast agents and chemical labeling substances) so as to be associated with the names (e.g., the substance name and the product name) of the substance.

In the first embodiment, the example is explained in which the database 39 is installed in the X-ray CT apparatus (in the console device 30); however, the first embodiment may be configured so that the database 39 is installed on the outside of the X-ray CT apparatus (the console device 30). In that situation, the console device 30 and the database 39 are connected to each other via a wired communication network or a wireless communication network.

FIG. 6 is a sequence chart of an example of the controlling process that is performed when the first setting method is implemented. As illustrated in FIG. 6, the controlling unit 38 queries the database 39 by transmitting thereto the parameter input by the operator. For example, the controlling unit 38 queries the database 39 with "substance name: AAA; characteristic energy: K absorption edge". In this situation, let us assume that the "substance name: AAA" represents the name of a xenon-based contrast agent. The database 39 conducts a search through the data stored therein by using "substance name: AAA; characteristic energy: K absorption edge" as search keywords and responds to the controlling unit 38 with a search result. For example, as illustrated in FIG. 6, because the "substance name: AAA" represents the name of the xenon-based contrast agent, the database 39 responds to the controlling unit 38 with "$E_K$=34.56 keV", which is the K absorption edge of xenon. If the database 39 is installed on the outside of the apparatus in which the controlling unit 38 is installed, the controlling unit 38 queries the database 39 installed on the outside, via a communication network.

In the example described above, the database 39 has a searching function. In other words, the controlling unit 38 requests the search for the characteristic energy value while using the parameter input by the operator as the keyword, whereas the database 39 conducts the search for the characteristic energy value by using the parameter appended to the query from the controlling unit 38 as the keyword and responds with the search result. If no data that corresponds to the parameter is present as a result of the search, the database 39 responds with a message such as "Not Found", for example.

The first embodiment may also be configured so that the controlling unit 38 conducts the search. In that situation, the controlling unit 38 conducts the search in the database 39 by using the parameter input by the operator as a keyword and obtains a characteristic energy value (e.g., the K absorption edge) that is unique to the substance corresponding to the parameter.

Further, in the explanation above, the example is explained in which the type of energy component is used together with the substance name as the parameter for the search; however, the first embodiment may be configured so that a substance name or a product name is used as a parameter for the search, but the type of characteristic energy is not used as a parameter for the search. In that situation, the database 39 responds to the controlling unit 38 with multiple types of characteristic energy values, so that the display device 32 displays, under the control of the controlling unit 38, a table showing a plurality of characteristic energy values with an indication of the types, for example. The operator refers to the table and designates one of the characteristic energy values to be used for identifying the substance, by using the input device 31 or the like.

When having obtained the characteristic energy value indicating the X-ray absorption characteristics of the substance designated by the operator as a result of the process described above, as illustrated in FIG. 6, the controlling unit 38 sets a plurality of energy discrimination regions having different granularity levels and being centered on the characteristic energy value, as the first setting method. Specifically, in an energy region positioned near the characteristic energy value, the controlling unit 38 sets energy discrimination regions having a fine granularity level. In contrast, in an energy region other than the energy region positioned near the characteristic energy value, the controlling unit 38 sets energy discrimination regions having a coarse granularity level.

An example of the energy dividing set that is set by implementing the first setting method will be explained, with reference to FIG. 7. FIG. 7 illustrates an example of an energy dividing set that is set by implementing the first setting method, when difference image data is generated by using the K absorption edge "$E_K$=34.56 keV" of xenon. In FIG. 7, the vertical axis for the X-ray absorption spectrum expresses a mass attenuation coefficient.

In FIG. 7, "0 to 9" represent ten energy discrimination regions "ER0 to ER9", which structure the energy dividing set that has been set by the controlling unit 38. As illustrated in FIG. 7, the controlling unit 38 sets "ER4, ER5, ER6, and ER7" each having a smaller width, in the energy region that is positioned near and is centered on the K absorption edge "$E_K$=34.56 keV" of xenon. In the example illustrated in FIG. 7, the boundary between ER5 and ER6 corresponds to the K absorption edge "$E_K$=34.56 keV" of xenon.

After that, as illustrated in FIG. 7, the controlling unit 38 sets "ER0, ER1, ER2, and ER3" and "ER8 and ER9" each having a larger width than the width of each of "ER4 to ER7", in the region other than the region of "ER4 to ER7". In the example illustrated in FIG. 7, the widths of the discrimination regions are arranged so as to satisfy: "ER0=ER1=ER2=ER9>ER3=ER8>ER4=ER5=ER6=ER7".

The X-ray absorption spectra of substances other than the substance of interest exhibit a smooth transition in the region positioned near the K absorption edge of the substance of interest. In order to efficiently eliminate the information about the substances other than xenon by performing the difference calculating process, it is desirable to make smaller the energy range used for calculating the difference. For this reason, with respect to the region containing the information required by the generation of the difference image data using the K absorption edge of xenon, the controlling unit 38 sets "ER4, ER5, ER6, and ER7" each having a smaller width, by making an adjustment so that the boundary between E5 and E6 corresponds to the K absorption edge of xenon.

In contrast, the region other than the region positioned near the K absorption edge of the substance of interest is not necessarily required by the generation of the difference image data using the K absorption edge. For this reason, the controlling unit 38 sets the energy discrimination regions each having a larger width, in the region other than "ER4 to ER7", which represent the region positioned near the K absorption edge of xenon.

After that, as illustrated in FIG. 6, the controlling unit 38 notifies the acquiring unit 14 of setting values related to the energy dividing set that has been set. The setting values are a plurality of threshold values used for allocating the pulse counting results with which the energy values are calculated, to the ten energy discrimination regions "ER0 to ER9". When a CT scan is started after the energy dividing set is set, the acquiring unit 14 allocates the counted values to each of the energy discrimination regions, as illustrated in FIG. 6.

FIG. 8 illustrates a bar graph in which X-ray photon energy values obtained as a result of discriminating the pulses output from the detector 13 are arranged along a time series. In the example illustrated in FIG. 8, the acquiring unit 14 acquires a counting result indicating that the counted value "C(ER0)" for "ER0" is "3"; the counted value "C(ER1)" for "ER1" is "4"; the counted value "C(ER2)" for "ER2" is "4"; and the counted value "C(ER3)" for "ER3" is "5".

Further, in the example illustrated in FIG. 8, the acquiring unit 14 acquires a counting result indicating that the counted value "C(ER4)" for "ER4" is "1"; the counted value "C(ER5)" for "ER5" is "2"; the counted value "C(ER6)" for "ER6" is "0"; and the counted value "C(ER7)" for "ER7" is "1". Furthermore, in the example illustrated in FIG. 8, the acquiring unit 14 acquires a counting result indicating that the counted value "C(ER8)" for "ER8" is "0"; and the counted value "C(ER9)" for "ER9" is "1".

The acquiring unit 14 acquires "C(ER0) to C(ER9)" for each of the X-ray tube phases and transmits the acquired counting results to the console device 30. After that, the image reconstructing unit 36 performs the image reconstructing process. For example, as illustrated in FIG. 7, the image reconstructing unit 36 reconstructs first image data 101 from projection data corresponding to a counting result of "C(ER4)+C(ER5)", according to an instruction from the controlling unit 38 or the operator. Further, for example, as illustrated in FIG. 7, the image reconstructing unit 36 reconstructs second image data 102 from projection data corresponding to a counting result of "C(ER6)+C(ER7)", according to an instruction from the controlling unit 38 or the operator. Furthermore, for example, as illustrated in FIG. 7, the image reconstructing unit 36 generates difference image data 103 by subtracting the first image data 101 from the second image data 102. The display device 32 then displays the difference image data 103, under the control of the controlling unit 38.

Further, for example, as illustrated in FIG. 7, the image reconstructing unit 36 may generate superimposed image data 104 obtained by superimposing the second image data 102 on the difference image data 103, under the control of the controlling unit 38. The difference image data 103 renders the region in which the xenon-based contrast agent is distributed. However, to enable the operator to recognize the region to which the distribution region corresponds, it is desirable to display the image data obtained by superimposing X-ray CT image data rendering the entire tissue morphology on the difference image data 103. In this situation, the X-ray CT image data to be superimposed may be the first image data 101 or may be X-ray CT image data reconstructed from projection data that corresponds to all of the counting results.

The first image data 101 may be reconstructed from projection data that corresponds to the counting result of "C(ER3) to C(ER5)" or from projection data that corresponds to the counting result of "C(ER0) to C(ER5)". Similarly, the second image data 102 may be reconstructed from projection data that corresponds to the counting result of "C(ER6) to C(ER8)" or from projection data that corresponds to the counting result of "C(ER6) to C(ER9)". Such changes may arbitrarily be made to the conditions by the operator who has referred the difference image data 103 and/or the superimposed image data 104.

Figure 10:
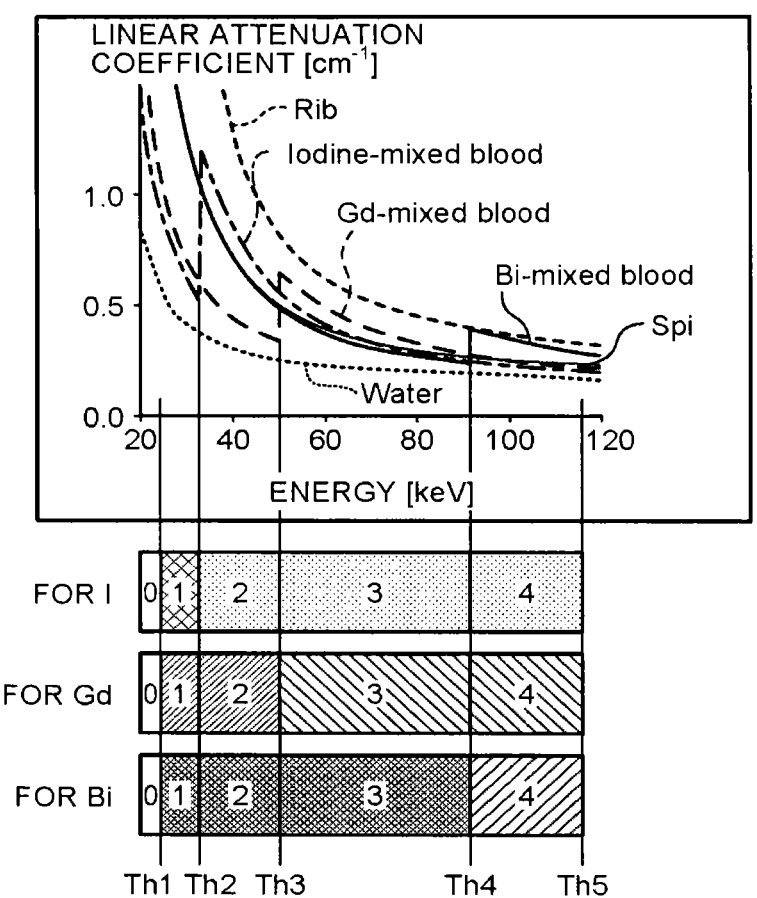
FIG. 10, FIG. 11A and FIG. 11B are drawings of examples of a second setting method implemented by the controlling unit according to the first embodiment.
Figure 11A:
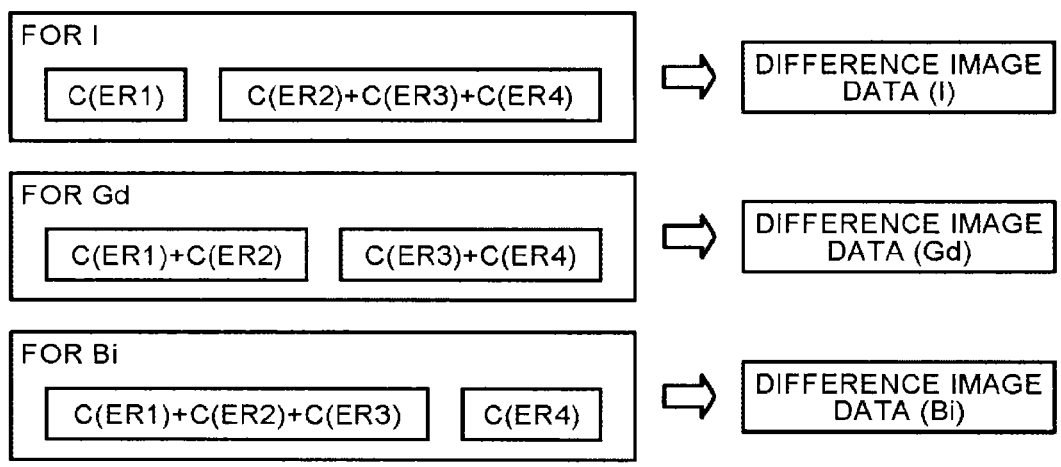
Figure 11B:
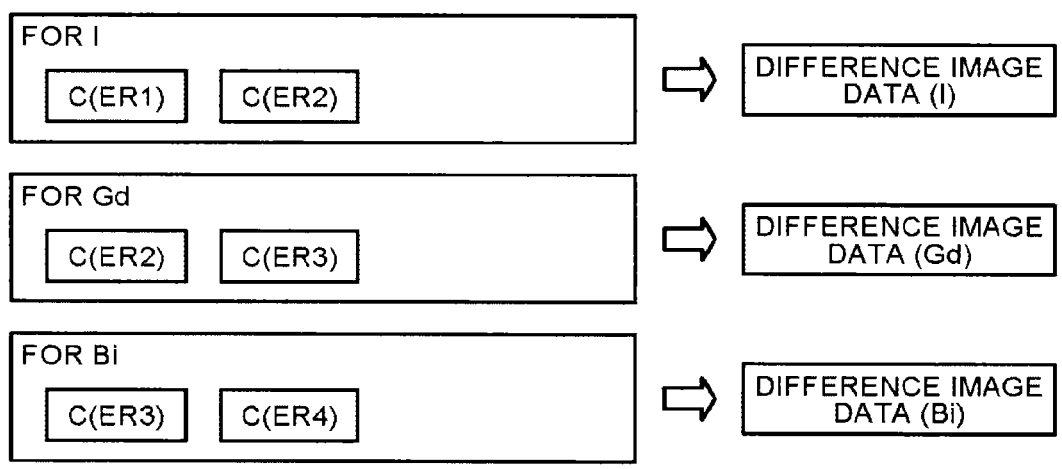
Figure 12:
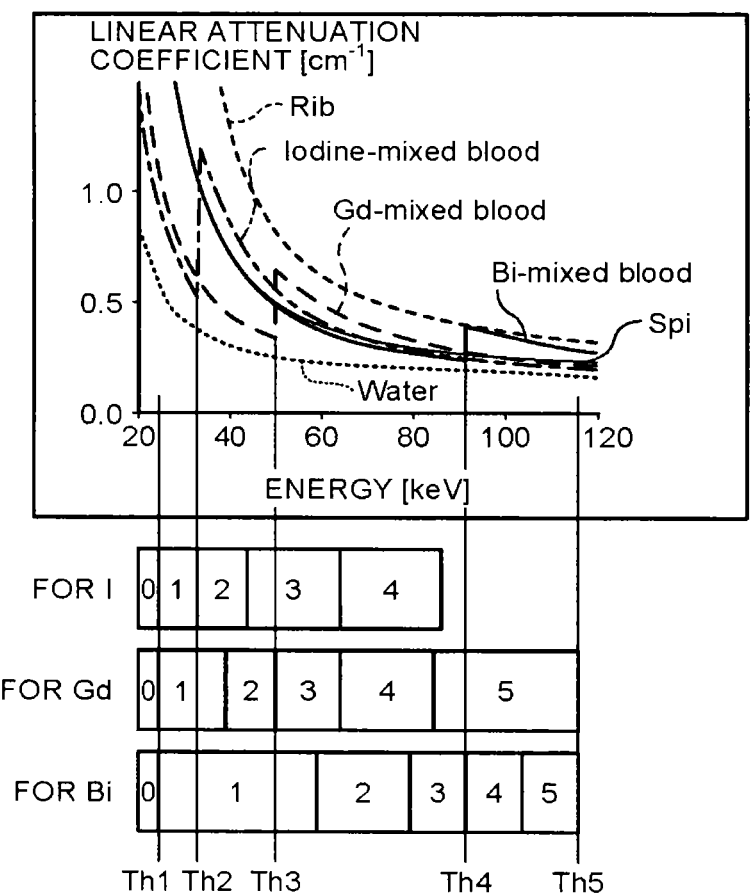
FIG. 12 is a drawing of an example of a third setting method implemented by the controlling unit according to the first embodiment.

Next, the second setting method and the third setting method will be explained, with reference to FIG. 9, FIG. 10, FIG. 11A, FIG. 11B, FIG. and FIG. 12. FIG. 9 is a drawing for explaining a controlling process performed by the controlling unit according to the first embodiment when a plurality of substances is designated. FIGS. 10, 11A, and 11B are drawings of examples of the second setting method implemented by the controlling unit according to the first embodiment. FIG. 12 is a drawing of an example of the third setting method implemented by the controlling unit according to the first embodiment.

FIG. 9 illustrates a sequence chart of an example of the controlling process that is performed when either the second setting method or the third setting method is implemented. As illustrated in FIG. 9, the controlling unit 38 queries the database 39 about the plurality of substances by transmitting thereto a plurality of parameters input by the operator. For example, the controlling unit 38 queries the database 39 with "substance name: A; characteristic energy: K absorption edge", "substance name: B; characteristic energy: K absorption edge", and "substance name: C; characteristic energy: K absorption edge". In this situation, let us assume that the "substance name: A" represents the name of an iodine-based contrast agent, whereas the "substance name: B" represents the name of a gadolinium-based contrast agent, and the "substance name: C" represents the name of a bismuth-based contrast agent.

The database 39 conducts a search through the data stored therein by using "substance name: A; characteristic energy: K absorption edge", "substance name: B; characteristic energy: K absorption edge", and "substance name: C; characteristic energy: K absorption edge" as search keywords and responds to the controlling unit 38 with a search result. As for "substance name: A; characteristic energy: K absorption edge", the database 39 responds to the controlling unit 38 with "$E_K$=33.16 keV", which is the K absorption edge of iodine, serving as a "threshold value: Th2". As for "substance name: B; characteristic energy: K absorption edge", the database 39 responds to the controlling unit 38 with "$E_K$=50.24 keV", which is the K absorption edge of gadolinium, serving as a "threshold value: Th3". As for "substance name: C; characteristic energy: K absorption edge", the database 39 responds to the controlling unit 38 with "$E_K$=90.55 keV", which is the K absorption edge of bismuth, serving as a "threshold value: Th4". In this situation, the controlling unit 38 may obtain "Th2, Th3, and Th4" by conducting a search in the database 39 or may receive "Th2, Th3, and Th4" from the operator.

After that, as illustrated in FIG. 9, the controlling unit 38 sets an energy dividing set for each of the substances and notifies the acquiring unit 14 of the setting values used for setting the energy dividing set for each of the substances. When a CT scan is started after the energy dividing set is set for each of the substances, the acquiring unit 14 allocates a counted value to each of the energy discrimination regions of each of the substances, as illustrated in FIG. 9.

When implementing the second setting method, if a plurality of substances are designated by the operator, the controlling unit 38 sets energy dividing sets by setting the plurality of energy discrimination regions while using the characteristic energy value indicating the X-ray absorption characteristics of each of the substances. For example, as illustrated in FIG. 10, the controlling unit 38 sets the plurality of energy discrimination regions by using "Th1", which is a lower-limit threshold value used for assessing a noise level, as well as "Th5", which is an upper-limit threshold value used for assessing an energy level unnecessary for the reconstructing process, together with "Th2, Th3, and Th4". In this situation, "Th1" and "Th5" are threshold values that are set uniquely to the system and are values that are set for the controlling unit 38 in advance. In other words, the controlling unit 38 sets four energy discrimination regions used for allocating the counting result, by using "Th2, Th3, and Th4", which are the threshold values unique to the three designated substances, respectively, as well as "Th1", which is the lower-limit threshold value unique to the system, and "Th5", which is the upper-limit threshold value unique to the system.

For example, the controlling unit 38 sets "ER(1): Th1≤E<Th2" indicated as "1" in FIG. 10, "ER(2): Th2≤E<Th3" indicated as "2" in FIG. 10, "ER(3): Th3≤E<Th4" indicated as "3" in FIG. 10, and "ER(4): Th4≤E<Th5" indicated as "4" in FIG. 10. In this situation, the controlling unit 38 makes a setting so that the counting result of "ER(0): E<Th1" indicated as "0" in FIG. 10 is discarded. Further, the controlling unit 38 makes a setting so that the counting result of "ER(5): Th5<E", which is not shown in FIG. 10, is discarded.

After that, the controlling unit 38 sets the energy dividing set for each of the plurality of substances, by further bundling the plurality of energy discrimination regions into a plurality of energy discrimination regions having a coarse granularity level in accordance with the characteristic energy value of each of the plurality of substances. For example, as illustrated in FIG. 10, by using "Th1, Th2, and Th5", the controlling unit 38 sets the two energy discrimination regions "ER(1)" and "ER(2)+ER(3)+ER(4)" as an energy dividing set for I (iodine). Further, for example, as illustrated in FIG. 10, by using "Th1, Th3, and Th5", the controlling unit 38 sets the two energy discrimination regions "ER(1)+ER(2)" and "ER(3)+ER(4)" as an energy dividing set for Gd (gadolinium). Further, for example, as illustrated in FIG. 10, by using "Th1, Th4, and Th5", the controlling unit 38 sets the two energy discrimination regions "ER(1)+ER(2)+ER(3)" and "ER(4)" as an energy dividing set for Bi (bismuth).

In this situation, the counted value of "ER(1)" will be referred to as "C(ER1)"; the counted value of "ER(2)" will be referred to as "C(ER2)"; the counted value of "ER(3)" will be referred to as "C(ER3)"; and the counted value of "ER(4)" will be referred to as "C(ER4)".

When the energy dividing sets illustrated in FIG. 10 have been set, the acquiring unit 14 transmits "C(ER1)" and an addition value "C(ER2)+C(ER3)+C(ER4)" to the console device 30 as a counting result of I, as illustrated in FIG. 11A. Further, the acquiring unit 14 transmits an addition value "C(ER1)+C(ER2)" and an addition value "C(ER3)+C(ER4)" to the console device 30 as a counting result of Gd, as illustrated in FIG. 11A. Further, the acquiring unit 14 transmits an addition value "C(ER1)+C(ER2)+C(ER3)" and "C(ER4)" to the console device 30 as a counting result of Bi, as illustrated in FIG. 11A.

As a result, as illustrated in FIG. 11A, the image reconstructing unit 36 generates difference image data (I) from the counting result of I, generates difference image data (Gd) from the counting result of Gd, and generates difference image data (Bi) from the counting result of Bi.

Alternatively, the first embodiment may be configured so that, for example, the controlling unit 38 notifies the acquiring unit 14 of an energy dividing set made up of "ER(1), ER(2), ER(3), and ER(4)". In that situation, the acquiring unit 14 transmits "C(ER1), C(ER2), C(ER3), and C(ER4)". After that, according to an instruction from the controlling unit 38, the image reconstructing unit 36 divides the projection data of "C(ER1), C(ER2), C(ER3), and C(ER4)" into projection data of I, projection data of Gd, and projection data of Bi and generates the difference image data (I), the difference image data (Gd), and the difference image data (Bi).

In either of these examples, it is possible to secure the discrimination capability realized by using the difference image data of each of the substances and to reduce the data amount. Further, for example, the operator who has referred the pieces of difference image data may change the condition so that a difference calculating process is performed only in such energy discrimination regions that are positioned before and after the K absorption edge of each of the substances. In that situation, as illustrated in FIG. 11B, the acquiring unit 14 transmits "C(ER1)" and "C(ER2)" to the console device 30 as a counting result of I. Further, as illustrated in FIG. 11B, the acquiring unit 14 transmits "C(ER2)" and "C(ER3)" to the console device 30 as a counting result of Gd. In addition, as illustrated in FIG. 11B, the acquiring unit 14 transmits "C(ER3)" and "C(ER4)" to the console device 30 as a counting result of Bi.

It should be noted, however, that in the example illustrated in FIG. 11B, because the amount of information for the imaging process is reduced, there is a possibility that the discrimination capability realized by using the difference image data may become low. Accordingly, for example, the operator may select whether or not the process illustrated in FIG. 11B should be performed. In order to secure the discrimination capability realized by using the difference image data, it is desirable to perform the process illustrated in FIG. 11A.

Next, the third setting method will be explained. When implementing the third setting method, if a plurality of substances is designated by the operator, the controlling unit 38 obtains the characteristic energy values (Th2, Th3, and Th4) of the substances and sets the energy dividing set for each of the substances by implementing the first setting method. Together with the characteristic energy values of the substances, the controlling unit 38 also uses Th1 and Th5 described above. For example, as illustrated in FIG. 12, the controlling unit 38 sets an energy dividing set for I by setting energy discrimination regions having a fine granularity level in a region centered on the Th2 value (see "1" and "2" in FIG. 12) and by setting energy discrimination regions having a coarse granularity level in the region other than that region (see "3" and "4" in FIG. 12).

Further, as illustrated in FIG. 12, the controlling unit 38 sets an energy dividing set for Gd by setting energy discrimination regions having a fine granularity level in a region centered on the Th3 value (see "2" and "3" in FIG. 12) and by setting energy discrimination regions having a coarse granularity level in the region other than that region (see "1", "4", and "5" in FIG. 12). Further, as illustrated in FIG. 12, the controlling unit 38 sets an energy dividing set for Bi by setting energy discrimination regions having a fine granularity level in a region centered on the Th4 value (see "3" and "4" in FIG. 12) and by setting energy discrimination regions having a coarse granularity level in the region other than that region (see "1", "2", and "5" in FIG. 12). After that, the controlling unit 38 notifies the acquiring unit 14 of the energy dividing set for each of the substances illustrated in FIG. 12 and causes a CT scan to be started.

In the third setting method illustrated in FIG. 12, the acquiring unit 14 needs to perform the energy discrimination process by further using seven threshold values in addition to the five threshold values "Th1 to Th5". To cope with this situation, the controlling unit 38 may make an adjustment so as to reduce the number of threshold values used by the acquiring unit 14 in addition to the five threshold values "Th1 to Th5", by setting energy discrimination regions for each of the substances within a range that accommodates the rule of the first setting method.

The controlling unit 38 according to the first embodiment further stores the setting values (the plurality of threshold values) used for setting the energy dividing sets of which the acquiring unit 14 was notified, in a predetermined storage unit so as to be associated with the corresponding substances. The predetermined storage unit may be database 39. For example, when having implemented the first setting method, the controlling unit 38 requests the database 39 to store the setting values therein, as illustrated in FIG. 6. As a result, for example, the database 39 stores the setting values used for setting "ER0 to ER9" so as to be associated with "substance name: AAA" or the like. As a result of this process, if a designation of "substance name: AAA" is received from the operator again, the database 39 returns the setting values for "ER0 to ER9", in response to a query from the controlling unit 38. Alternatively, as the predetermined storage unit, the controlling unit 38 may use an internal memory installed in the apparatus in which the controlling unit 38 is installed.

Further, when having implemented the second setting method or the third setting method, for example, the controlling unit 38 requests the database 39 to store the setting values of each of the substances, as illustrated in FIG. 9. As a result, for example, the database 39 stores the setting values for "ER(1)" and "ER(2)+ER(3)+ER(4)" so as to be associated with "substance name: I". Further, for example, the database 39 stores the setting values for "ER(1)+ER(2)" and "ER(3)+ER(4)" so as to be associated with "substance name: Gd". Furthermore, for example, the database 39 stores the setting values for "ER(1)+ER(2)+ER(3)" and "ER(4)" so as to be associated with "substance name: Bi".

Because the energy dividing sets are set by using the first, the second, or the third setting method as described above, the acquiring unit 14 is able to acquire the counting result in which the information required by the imaging process of the substances of interest of the operator is secured. Because the energy dividing sets are set, the amount of the data in the counting result in this situation is significantly reduced from that in the energy dividing set illustrated in FIG. 4B, for example.

Next, the GUI that is displayed to enable the operator to perform input operations, so that the controlling unit 38 is able to perform the processes described above, will be explained, with reference to FIG. 13A, FIG. 13B, FIG. 13C, FIG. 13D, and FIG. 14. FIG. 13A, FIG. 13B, FIG. 13C, FIG. 13D, and FIG. 14 are drawings of examples of the GUI according to the first embodiment.

Figure 13A:
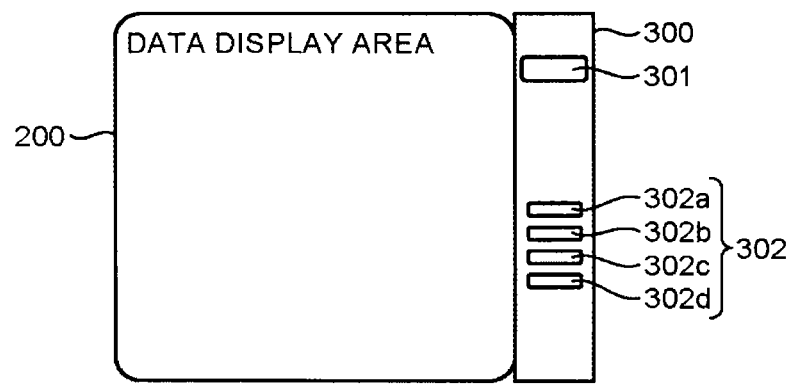
FIG. 13A, FIG. 13B, FIG. 13C, FIG. 13D and FIG. 14 are drawings of examples of a Graphical User Interface (GUI) according to the first embodiment.

For example, under the control of the controlling unit 38, the display device 32 displays an input-purpose GUI 300 used by the operator to input a parameter that makes it possible to identify a substance, together with a "data display area 200" used for displaying image data, as illustrated in FIG. 13A.

Figure 13B:

In the input-purpose GUI 300 illustrated in FIG. 13A, a box 301 used by the operator to input the parameter is provided. After selecting the box 301 with the mouse, the operator inputs a parameter "AAA", for example, into the box 301 by using the keyboard, as illustrated in FIG. 13B. Subsequently, after checking the input parameter, the operator presses a search-request-purpose shortcut key, for example. As a result, the searching process and the controlling process explained with reference to FIG. 6 to FIG. 8 are automatically started.

Figure 13C:

Further, after selecting the box 301 with the mouse, the operator inputs a parameter "I, Gd, Bi", for example, into the box 301 by using the keyboard, as illustrated in FIG. 13C. Subsequently, after checking the input parameter, the operator presses the search-request-purpose shortcut key, for example. As a result, the searching process and the controlling process explained with reference to FIG. 9 to FIG. 11B are automatically started.

Further, under the control of the controlling unit 38, the display device 32 displays an operation button used for reading the setting values of which the acquiring unit 14 was informed by the controlling unit 38. The controlling unit 38 has stored the setting values (the plurality of threshold values) used for setting the energy dividing sets of which the acquiring unit 14 was informed, in the database 39 or an internal memory, so as to be associated with the corresponding substances. Thus, in the input-purpose GUI 300 illustrated in FIG. 13A, a shortcut-purpose operation button group 302 (i.e., operation buttons 302a to 302d) used for causing a process to be performed with the use of the previously-set setting values are provided.

Figure 13D:

For example, as illustrated in FIG. 13D, the operation button 302a is an operation button for causing the controlling unit 38 to obtain, from the database 39 or the internal memory, the setting values used by the controlling unit 38 to set the energy dividing set for I, the energy dividing set for Gd, and the energy dividing set for Bi. As illustrated in FIG. 13D, for example, the operator moves a cursor to the operation button 302a showing the text "I, Gd, Bi" and clicks on the operation button 302a with the mouse. As a result, it is possible to start a CT scan for acquiring the difference image data for each of the substances "I, Gd, and Bi".

In the example described above, the shortcut buttons displayed as the operation button group 302 are automatically generated and displayed in the input-purpose GUI 300, as history information of the operations performed by the operator while using the box 301. In other words, the shortcut-purpose operation button group 302 is generated and displayed for the purpose of enabling a medical doctor to make a designation again without using the box 301, when performing an imaging process to identify chemical substances that have a history of having actually been used an a past analysis. It is sufficient if the one or more energy dividing sets that are set by implementing the first, the second, or the third setting method are set prior to a CT scan. Thus, the first embodiment may be configured in such a manner that the shortcut-purpose operation button group 302 is set for such chemical substances that have a possibility of being frequently used in analyses.

For such chemical substances that have a possibility of being frequently used in analyses, for example, a medical doctor or a maintenance person may perform an input operation in advance so as to cause the controlling unit 38 to set the energy dividing sets, so that the setting values obtained therefrom are stored in the database 39 or an internal memory. Accordingly, the controlling unit 38 causes shortcut buttons to be generated and displayed for such chemical substances that have a possibility of being frequently used in analyses. Alternatively, instead of obtaining the setting values in advance, the shortcut buttons for the chemical substances that have a possibility of being frequently used in analyses may be used by the controlling unit 38 for the purpose of querying the database 39 about characteristic energy values of the corresponding substances by using a click operation on the shortcut buttons as a trigger.

Further, when the first setting method is implemented as explained with reference to FIG. 7, according to a designation from the operator, the first image data 101 may be reconstructed from the counting result of "C(ER4)+C(ER5)", whereas the second image data 102 may be reconstructed from the counting result of "C(ER6)+C(ER7)". In that situation, the data required by the imaging process performed in response to a request from the operator is represented by the two energy discrimination regions such as "ER4+ER5" and "ER6+ER7". Further, when the second setting method illustrated in FIG. 11B is implemented, the energy dividing set for each of the substances will be changed.

Further, the measured energy values may not necessarily be consistent with the true energy values, due to various factors such as the physical properties of the detector 13 and the acquiring unit 14. Thus, for example, the threshold values (e.g., the K absorption edge values) set by the controlling unit 38 may not be optimal setting values. In that situation, the operator may change the setting values that were set by the controlling unit 38.

As explained above, in the first embodiment, the operator may make a change to the condition (the energy dividing set) that was set by the controlling unit 38 for an imaging purpose. When performing an imaging process of a substance of which the condition was changed in the past, it would be a burden on the operator to need to manually make a change again to the condition that was automatically set by the controlling unit 38 for the imaging purpose. To cope with this situation, if an energy dividing set has been changed on the basis of a change made to the condition by the operator, the controlling unit 38 stores the setting values used for resetting the energy dividing set in the database 39 or an internal memory, so as to be associated with the corresponding substance. Further, the controlling unit 38 causes the display device 32 to display an operation button used for reading the setting values used for resetting the energy dividing set.

Figure 14:
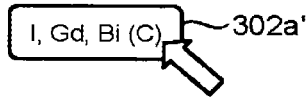

For example, when a change is made to the condition as illustrated in FIG. 11B, the controlling unit 38 stores the setting values used for setting the energy dividing set "ER(1) and ER(2)" for I, the setting values used for setting the energy dividing set "ER(2) and ER(3)" for Gd, and the setting values used for setting the energy dividing set "ER(3) and ER(4)" for Bi. After that, as a shortcut button for reading the setting values based on the change made to the condition illustrated in FIG. 11B, the controlling unit 38 causes an "operation button 302a'" to be displayed as illustrated in FIG. 14. For example, as illustrated in FIG. 14, the "operation button 302a'" has "I, Gd, Bi (C)" written thereon, so as to clearly indicate that this button is a shortcut button used for reading the setting values customized by the operator.

Figure 15:
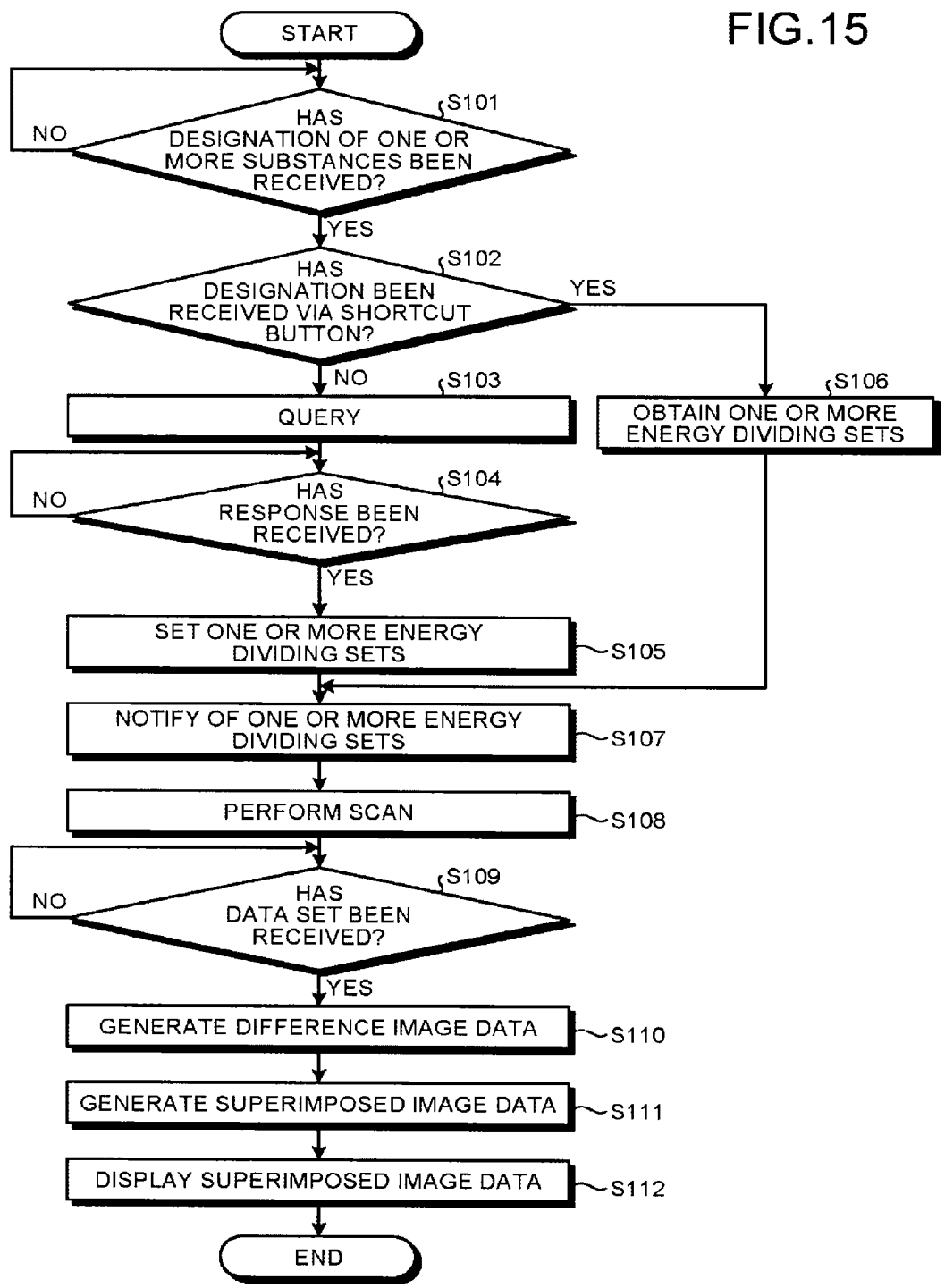
FIG. 15 is a flowchart for explaining an exemplary process performed by the X-ray CT apparatus according to the first embodiment.

Next, a process performed by the X-ray CT apparatus according to the first embodiment will be explained, with reference to FIG. 15. FIG. 15 is a flowchart for explaining an exemplary process performed by the X-ray CT apparatus according to the first embodiment. The flowchart presented in FIG. 15 illustrates a process that is performed when the setting values corresponding to a shortcut button have already been stored in an internal memory.

As illustrated in FIG. 15, the controlling unit 38 included in the X-ray CT apparatus according to the first embodiment judges whether a designation of one or more substances has been received from the operator (step S101). If no designation has been received (step S101: No), the controlling unit 38 waits until a designation of one or more substances has been received.

On the contrary, if a designation of one or more substances has been received (step S101: Yes), the controlling unit 38 judges whether the designation of the one or more substances has been received via a shortcut button (step S102). If the designation of the one or more substances was received via a shortcut (step S102: Yes), the controlling unit 38 obtains, from the internal memory, one or more energy dividing sets that have already been set on the basis of the characteristic energy values (step S106).

On the contrary, if the designation was not received via a shortcut (step S102: No), the controlling unit 38 queries the database 39 (step S103) and judges whether a response has been received (step S104). If no response has been received (step S104: No), the controlling unit 38 waits until a response is received.

On the contrary, if a response has been received (step S104: Yes), the controlling unit 38 sets the one or more energy dividing sets (step S105). If the response does not show any characteristic energy values, the controlling unit 38 determines that the database 39 has not registered therein any analytical chemical data of the substances of interest of the operator and therefore ends the process. Alternatively, the controlling unit 38 may query again to an external database.

Subsequently, after the process at step S105 or step S106, the controlling unit 38 notifies the acquiring unit 14 of the one or more energy dividing sets (step S107). After that, the controlling unit 38 causes the gantry device 10 to perform a CT scan, via the scan controlling unit 33 (step S108). Subsequently, the controlling unit 38 judges whether a data set of counting results acquired on the basis of the energy dividing sets has been received (step S109). If the data set has not been received (step S109: No), the controlling unit 38 waits until the data set is received.

On the contrary, if the data set has been received (step S109: Yes), the image reconstructing unit 36 generates difference image data under the control of the controlling unit 38 (step S110), and further generates superimposed image data (step S111).

After that, under the control of the controlling unit 38, the display device 32 displays the superimposed image data (step S112), and the process is ended.

As explained above, according to the first embodiment, the optimal energy dividing sets are actively set in accordance with the X-ray absorption characteristics of each of the substances by implementing one of the first, the second, and the third setting methods. In other words, according to the first embodiment, the controlling unit 38 sets such an energy dividing set that is structured by the plurality of energy discrimination regions capable of securing the information required by the imaging process of the substance of interest of the operator, while keeping the number of energy discrimination regions small. Consequently, according to the first embodiment, it is possible to reduce the amount of the data required by the imaging process, while securing the data required by the imaging process of the substance of interest of the operator.

Further, according to the first embodiment, the energy dividing sets are set, and also, the setting values thereof are stored, during the processes performed in advance, and further, the shortcut buttons used for reading the already-obtained setting values are displayed. Further, the setting values and the shortcut buttons may be updated or added in accordance with the changes made to the condition by the operator. Consequently, according to the first embodiment, it is possible to simplify the operations of the operator that are required by the imaging process of the substances of interest.

The method for setting the energy dividing sets according to the first embodiment is not limited to the setting methods described above. For example, when being actually measured, a characteristic energy value indicating the X-ray absorption characteristics of a substance such as the K absorption edge is expected to fluctuate within a certain range. In other words, the characteristic energy values obtained from the information registered in the database 39 are each an ideal value obtained from an ideal measuring process. Thus, measured values obtained from actual measuring processes may be different from the ideal values. For this reason, to discriminate a substance of interest without fail, for example, it may be preferable to determine the energy regions positioned before and after the K absorption edge as insensitive regions. Accordingly, when implementing any of the first, the second, and the third setting methods described above, the controlling unit 38 may apply thereto any of the modified examples described below.

When implementing the first setting method because a single substance is designated by the operator, the controlling unit 38 sets an energy dividing set in a region excluding the regions positioned before and after the characteristic energy value. For example, of the energy discrimination regions "ER0 to ER9" illustrated in FIG. 7, the controlling unit 38 sets the energy discrimination regions "ER5" and "ER6" that are positioned before and after the K absorption edge "$E_K$=34.56 keV" of xenon to be insensitive regions from which the counted values are not acquired.

In that situation, for example, the first image data 101 is reconstructed on the basis of the counting result of "C(ER4)" or the counting result of "C(ER3) and C(ER4)" or the counting result of "C(ER0) to C(ER4)". Further, for example, the second image data 102 is reconstructed on the basis of the counting result of "C(ER7)" or the counting result of "C(ER7) and C(ER8)" or the counting result of "C(ER7) to C(ER9)". According to the modified example of the first setting method described above, it is possible to set an energy dividing set that makes it possible to discriminate a xenon-based contrast agent with an emphasis thereon, even if the measured value of the K absorption edge of xenon fluctuates away from the ideal value "34.56 keV", for example. As a result, according to this modified example, it is possible to obtain difference image data 103 that makes it possible to identify the xenon-based contrast agent without fail.

In contrast, when implementing the second setting method or the third setting method because a plurality of substances are designated by the operator, the controlling unit 38 sets an energy dividing set for each of the plurality of substances in a region excluding the regions positioned before and after the characteristic energy value of each of the plurality of substances. For example, when setting the energy dividing sets illustrated in FIG. 10 and FIG. 12, the controlling unit 38 sets the region "'Th2−d2' to 'Th2+d2#'" positioned before and after Th2, the region "'Th3−d3' to 'Th3+d3#'" positioned before and after Th3, and the region "'Th4−d4' to 'Th4+d4#'" positioned before and after Th4 each to be an insensitive region. According to this modified example of the second setting method and the third setting method, it is also possible to set the energy dividing sets that make it possible to discriminate the contrast agents with an emphasis thereon, even if the measured value of the K absorption edge of each contrast agent fluctuates away from the ideal value thereof. As a result, according to this modified example, it is possible to obtain a group of difference image data that makes it possible to identify each of the plurality of types of contrast agents without fail.

The values used for setting the insensitive regions in the modified examples above may be set for the controlling unit 38 as an initial setting or may manually be set by the operator. Further, the values used for setting the insensitive regions in the modified examples described above may manually be changed by the operator. Further, the values used for setting the insensitive regions in the modified examples described above may automatically be changed by the controlling unit 38 on the basis of information about data acquisition amounts or about measuring errors for absorption edges. Further, for example, the operator may arbitrarily select whether the modified examples described above should be implemented.

Second Embodiment

The acquiring unit 14 according to the first embodiment needs to perform the energy discrimination process in accordance with the energy dividing sets that are actively changed and set by the controlling unit 38. In other words, the acquiring unit 14 needs to dynamically change the energy discrimination, by using the plurality of threshold values that are changed in accordance with the characteristic energy value of the substance serving as a processing target.

Figure 16:
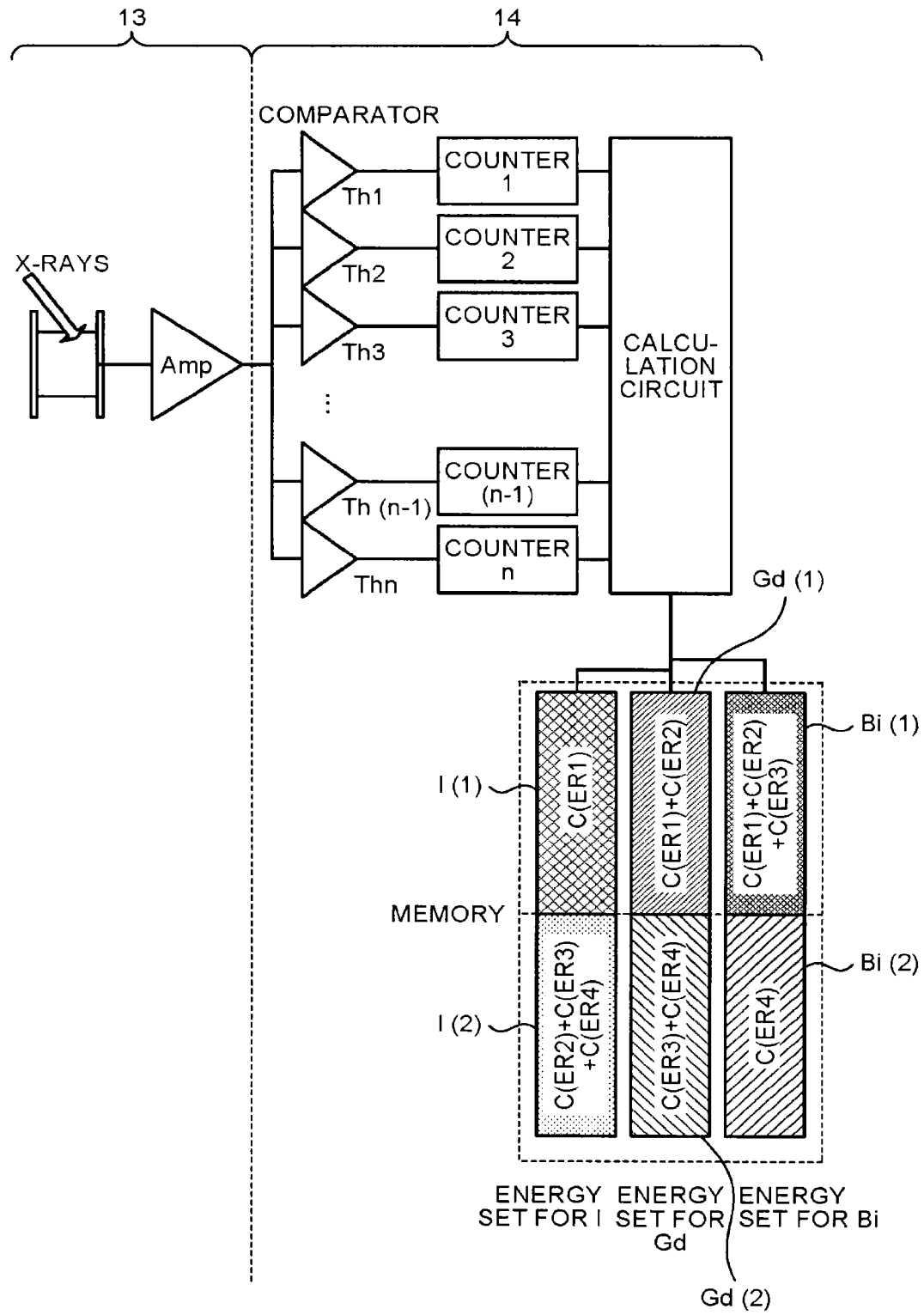
FIG. 16 is a drawing of a first exemplary configuration of the detector and the acquiring unit illustrated in FIG. 1.
Figure 17:
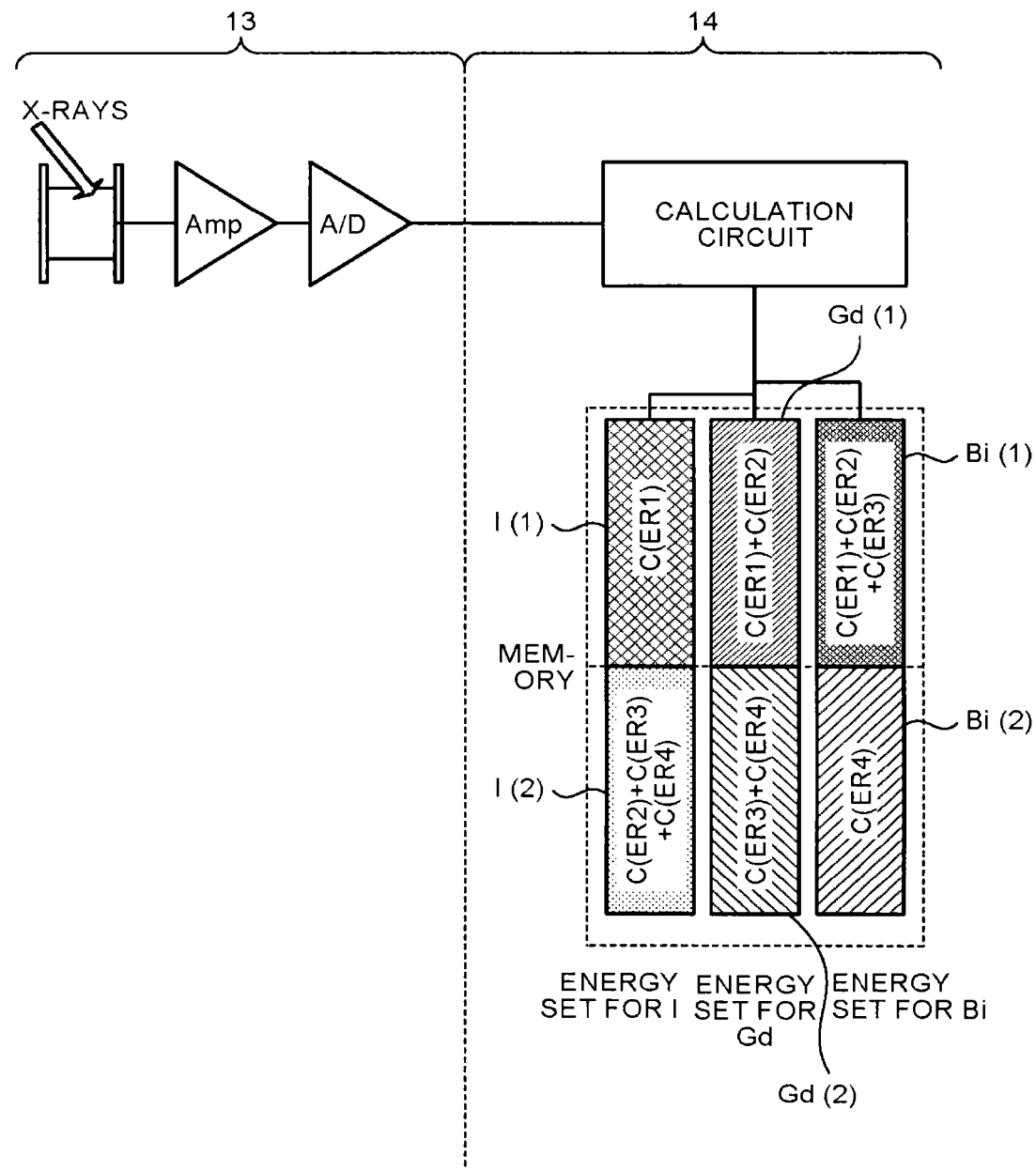
FIG. 17 is a drawing of a second exemplary configuration of the detector and the acquiring unit illustrated in FIG. 1.
Figure 18:
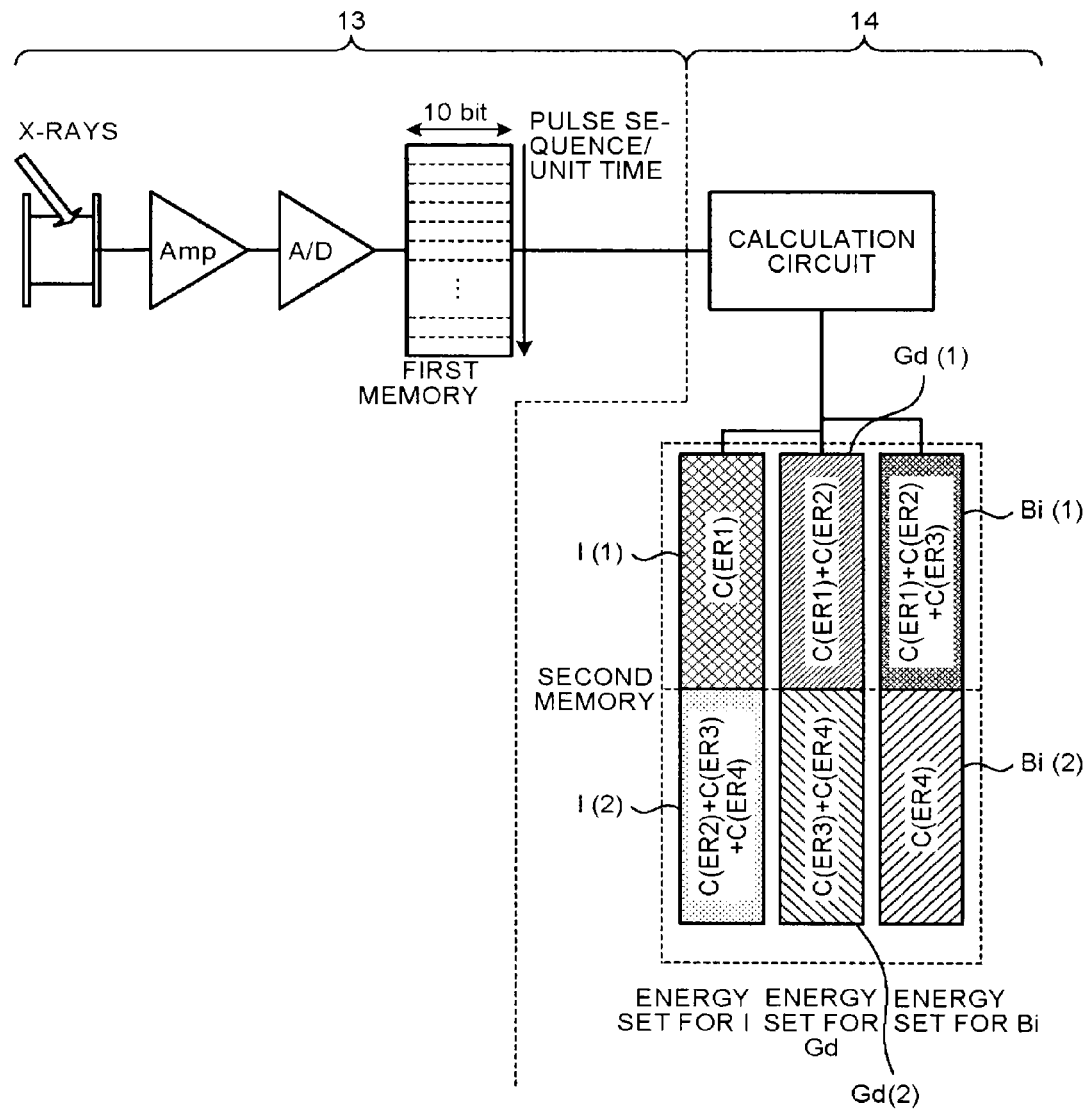
FIG. 18 is a drawing of a third exemplary configuration of the detector and the acquiring unit illustrated in FIG. 1.

Thus, in a second embodiment, specific exemplary configurations of the detector 13 and the acquiring unit 14 that make it possible to perform the energy discrimination process in accordance with the energy dividing sets that are set according to the first embodiment will be explained, with reference to FIG. 16, FIG. 17, and FIG. 18. FIG. 16 is a drawing of a first exemplary configuration of the detector and the acquiring unit illustrated in FIG. 1. FIG. 17 is a drawing of a second exemplary configuration of the detector and the acquiring unit illustrated in FIG. 1. FIG. 18 is a drawing of a third exemplary configuration of the detector and the acquiring unit illustrated in FIG. 1.

In the following sections, examples will be explained in which the three energy dividing sets for I, Gd, and Bi explained with reference to FIG. 10 have been set so that the acquiring unit 14 acquires the energy sets for I, Gd, and Bi illustrated in FIG. 11A.

First, the first exemplary configuration will be explained, with reference to FIG. 16. The "Amp" in FIG. 16 denotes an amplifier connected to each of the detecting elements 131 included in the detector 13. The "Amp" illustrated in FIG. 16 amplifies a signal output by each of the detecting elements 131 and transmits the amplified signal to the acquiring unit 14. As illustrated in FIG. 16, the acquiring unit 14 includes comparators of which the total number is equal to N, as well as counters (counter 1, counter 2, counter 3, ..., counter (n−1), and counter n) of which the total number is equal to N, each of the counters being connected to a different one of the N comparators. Each of the N comparators has set therein a different one of the threshold values (Th1, Th2, Th3, . . . , Th(n−1), and Thn). The controlling unit 38 is able to change and set an arbitrary threshold value in each of the comparators.

Each of the comparators illustrated in FIG. 16 generates one pulse if the signal output from the Amp exceeds the threshold value being set therein, so that the counter provided at the subsequent stage counts the number of pulses generated by the comparator at the preceding stage. In this situation, because the energy sets for I, Gd, and Bi illustrated in FIG. 11A are acquired, it means the threshold values "Th1 to Th5" are set for the five comparators.

Further, as illustrated in FIG. 16, one calculation circuit is installed at the stage subsequent to the N comparators, while a memory is installed at the stage subsequent to the calculation circuit. The memory illustrated in FIG. 16 has configured therein two storage areas (I(1) and I(2)) as areas for storing the energy set for I. Further, the memory illustrated in FIG. 16 has configured therein two storage areas (Gd(1) and Gd(2)) as areas for storing the energy set for Gd. Further, the memory illustrated in FIG. 16 has configured therein two storage areas (Bi(1) and Bi(2)) as areas for storing the energy set for Bi.

The calculation circuit illustrated in FIG. 16 is a multiplexer for the counters that simultaneously outputs the counted values of the counters respectively connected to the five comparators, to the plurality of storage areas configured in the memory, in accordance with the threshold values set in the comparators installed at the stage preceding the counters. For example, the calculation circuit outputs the counted value "C(ER1)" from the energy discrimination region "ER(1)" to I(1), Gd(1), and Bi(1). Further, the calculation circuit outputs the counted value "C(ER2)" from the energy discrimination region "ER(2)" to I(2), Gd(1), and Bi(1). Further, the calculation circuit outputs the counted value "C(ER3)" from the energy discrimination region "ER(3)" to I(2), Gd(2), and Bi(1). Furthermore, the calculation circuit outputs the counted value "C(ER4)" from the energy discrimination region "ER(4)" to I(2), Gd(2), and Bi(2).

As a result, as illustrated in FIG. 16, I(1) stores the counted value of "C(ER1)", whereas I(2) stores the counted value of "C(ER2)+C(ER3)+C(ER4)". Further, as illustrated in FIG. 16, Gd(1) stores the counted value of "C(ER1)+C(ER2)", whereas Gd(2) stores the counted value of "C(ER3)+C(ER4)". Furthermore, as illustrated in FIG. 16, Bi(1) stores the counted value of "C(ER1)+C(ER2)+C(ER3)", whereas Bi(2) stores the counted value of "C(ER4)".

Next, the second exemplary configuration will be explained with reference to FIG. 17. The "Amp" in FIG. 17 denotes an amplifier connected to all the detecting elements 131 included in the detector 13. The "A/D" in FIG. 17 denotes an analog/digital converter that converts a post-amplified analog electric signal output by the "Amp" into a digital signal. The "A/D" illustrated in FIG. 17 transmits the digital signal to the acquiring unit 14. As illustrated in FIG. 17, the acquiring unit 14 includes a calculation circuit and a memory. The calculation circuit illustrated in FIG. 17 is a circuit that has functions of a comparator, a counter, a selector, and a memory controller. As illustrated in FIG. 17, in the second exemplary configuration also, the memory has configured therein "I(1) and I(2)" as the areas for storing therein the energy set for I, "Gd(1) and Gd(2)" as the areas for storing therein the energy set for Gd, and "Bi(1) and Bi(2)" as the areas for storing therein the energy set for Bi.

The calculation circuit illustrated in FIG. 17 compares the output values of "A/D" by using the comparator function, and at the same time, determines the regions of the energy sets by using the selector function, and performs a count-up process by using the counter function. After that, for example, the calculation circuit illustrated in FIG. 17 writes a counted value per unit time into a corresponding area of the memory, by using the memory controller function. As a result, as illustrated in FIG. 17, the memory stores an energy set of each of the substances. The calculation circuit illustrated in FIG. 17 performs the processes using the comparator function, the selector function, the counter function, and the memory controller function, on the basis of the setting values notified by the controlling unit 38.

Next, the third exemplary configuration will be explained with reference to FIG. 18. The "Amp" in FIG. 18 denotes an amplifier connected to each of the detecting elements 131 included in the detector 13. The "A/D" in FIG. 18 denotes an analog/digital converter that converts a post-amplified analog electric signal output by the "Amp" into a digital signal. Further, a first memory illustrated in FIG. 18 stores digital signals per unit time that were output by the "A/D" as a 10-bit pulse sequence, for example. The first memory is, for example, a memory having a double-buffer structure that repeatedly performs "writing, resetting, and swapping".

The first memory outputs the pulse sequence per unit time to the acquiring unit 14. As illustrated in FIG. 18, the acquiring unit 14 includes a calculation circuit and a second memory. The calculation circuit illustrated in FIG. 18 is a circuit that has functions of a comparator, a counter, a selector, and a memory controller. As illustrated in FIG. 18, in the third exemplary configuration also, the second memory has configured therein "I(1) and I(2)" as the areas for storing the energy set for I, "Gd(1) and Gd(2)" as the areas for storing the energy set for Gd, and "Bi(1) and Bi(2)" as the areas for storing the energy set for Bi.

The calculation circuit illustrated in FIG. 18 compares the pulse sequences (the digital signals) per unit time by using the comparator function, and at the same time, determines the regions of the energy sets by using the selector function, and performs a count-up process by using the counter function. After that, for example, the calculation circuit illustrated in FIG. 18 writes a counted value per unit time into a corresponding area of the second memory, by using the memory controller function. As a result, as illustrated in FIG. 18, the second memory stores the energy set of each of the substances. The calculation circuit illustrated in FIG. 18 performs the processes using the comparator function, the selector function, the counter function, and the memory controller function, on the basis of the setting values notified by the controlling unit 38.

It is determined which one of the first, the second, and the third exemplary configurations should be selected, in accordance with the capability of the analog digital converter that is available, the scale of the circuit that can be accommodated in the gantry device 10, the price range of the X-ray CT apparatus, and the like.

The image processing explained in any of the exemplary embodiments described above is applicable to any image data in general that is based on a characteristic energy value unique to a substance and that can be generated from a photon counting CT. Further, the image processing explained in any of the exemplary embodiments described above may be performed by an image processing apparatus that is installed independently of the X-ray CT apparatus, as long as it is possible to obtain the counting results.

Further, the image processing methods described in the first and the second embodiments may be realized by causing a computer such as a personal computer or a workstation to execute an image processing computer program (hereinafter, an "image processing program") that is prepared in advance. The image processing program may be distributed via a network such as the Internet. Further, it is also possible to record the image processing program in a computer-readable recording medium such as a hard disk, a flexible disk (FD), a Compact Disk Read-Only Memory (CD-ROM), a Magneto-optical (MO) disk, a Digital Versatile Disk (DVD), or the like, so that a computer is able to read the program from the recording medium and to execute the read program.

As explained above, according to at least one aspect of the first and the second embodiments, it is possible to reduce the amount of the data required by the imaging process, while securing the data required by the imaging process of the substance of interest of the operator.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT apparatus comprising:
acquiring circuitry configured to count photons derived from X-rays that have passed through a subject and to acquire a result obtained by discriminating energy levels of the counted photons as a counting result; and
processing circuitry configured to set an energy dividing set by setting one or more energy discrimination regions having a fine granularity level in an energy region positioned near a characteristic energy value indicating the X-ray absorption characteristic of a substance designated by an operator and by setting one or more energy discrimination regions having a coarse granularity level in an energy region other than the energy region, to notify the acquiring circuitry of the energy dividing set, to receive the counting result acquired by the acquiring circuitry by allocating a counted value to each of a plurality of energy discrimination regions that are set in the energy dividing set, and to reconstruct image data by using the received counting result.

2. The X-ray CT apparatus according to claim 1, wherein the processing circuitry is configured to set the energy dividing set in a region excluding regions positioned before and after the characteristic energy value.

3. The X-ray CT apparatus according to claim 1, wherein, if a plurality of substances are designated by the operator, the processing circuitry is configured to set the energy dividing set by setting a plurality of energy discrimination regions according to a characteristic energy value indicating an X-ray absorption characteristic of each of the substances.

4. The X-ray CT apparatus according to claim 3, wherein the processing circuitry is configured to set the energy dividing set for each of the plurality of substances, by further bundling the plurality of energy discrimination regions with a plurality of energy discrimination regions having a coarse granularity level in accordance with the characteristic energy value of each of the plurality of substances.

5. The X-ray CT apparatus according to claim 4, wherein the processing circuitry is configured to set the energy dividing set for each of the plurality of substances in a region excluding regions positioned before and after the characteristic energy value of each of the plurality of substances.

6. The X-ray CT apparatus according to claim 1, wherein the processing circuitry is configured to set the energy dividing set prior to the acquisition of the counting result.

7. The X-ray CT apparatus according to claim 1, wherein the processing circuitry is configured to set the energy dividing set by using a data memory circuitry storing therein information about an X-ray absorption spectrum of each of a plurality of substances.

8. The X-ray CT apparatus according to claim 1, wherein the processing circuitry is configured to store setting values used for setting the energy dividing set into a predetermined storage circuitry so as to be associated with the corresponding substance and causes a display to display an operation button used for reading the setting values.

9. The X-ray CT apparatus according to claim 1, wherein, if the energy dividing set has been changed based on a condition change performed by the operator, the processing circuitry is configured to store setting values used for resetting the energy dividing set in a predetermined storage circuitry so as to be kept the corresponding substance and to cause a display to display an operation button used for reading the setting values.

10. An image processing apparatus comprising:
processing circuitry configured to set an energy dividing set by setting one or more energy discrimination regions having a fine granularity level in an energy region positioned near a characteristic energy value indicating the X-ray absorption characteristic of a substance designated by an operator and by setting one or more energy discrimination regions having a coarse granularity level in an energy region other than the energy region, to notify acquiring circuitry which is configured to count photons derived from X-rays that have passed through a subject and acquire a result obtained by discriminating energy levels of the counted photons as a counting result, of the energy dividing set, to receive the counting result acquired by the acquiring circuitry by allocating a counted value to each of a plurality of energy discrimination regions that are set in the energy dividing set, and to reconstruct image data by using the received counting result.

11. An image processing method comprising:
performing a process by processing circuitry to set an energy dividing set by setting one or more energy discrimination regions having a fine granularity level in an energy region positioned near a characteristic energy value indicating the X-ray absorption characteristic of a substance designated by an operator and by setting one or more energy discrimination regions having a coarse granularity level in an energy region other than the energy region, to notify acquiring circuitry which is configured to count photons derived from X-rays that have passed through a subject and acquire a result obtained by discriminating energy levels of the counted photons as a counting result, of the energy dividing set, to receive the counting result acquired by the acquiring circuitry by allocating a counted value to each of a plurality of energy discrimination regions that are set in the energy dividing set, and to reconstruct image data by using the received counting result.

* * * * *